US009075026B2

(12) United States Patent
Urano et al.

(10) Patent No.: US 9,075,026 B2
(45) Date of Patent: Jul. 7, 2015

(54) DEFECT INSPECTION DEVICE AND DEFECT INSPECTION METHOD

(75) Inventors: Takahiro Urano, Ebina (JP); Kaoru Sakai, Yokohama (JP); Toshifumi Honda, Yokohama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 528 days.

(21) Appl. No.: 13/387,369

(22) PCT Filed: Aug. 30, 2010

(86) PCT No.: PCT/JP2010/005312
§ 371 (c)(1),
(2), (4) Date: May 16, 2012

(87) PCT Pub. No.: WO2011/036846
PCT Pub. Date: Mar. 31, 2011

(65) Prior Publication Data
US 2012/0229618 A1    Sep. 13, 2012

(30) Foreign Application Priority Data

Sep. 28, 2009  (JP) ................................. 2009-221903
Jun. 23, 2010  (JP) ................................. 2010-142177

(51) Int. Cl.
*G06K 9/60*    (2006.01)
*G01N 21/95*   (2006.01)
(Continued)

(52) U.S. Cl.
CPC .... *G01N 21/9501* (2013.01); *G01N 2021/8825* (2013.01); *G01N 2021/9513* (2013.01);
(Continued)

(58) Field of Classification Search
None
See application file for complete search history.

(56) References Cited

U.S. PATENT DOCUMENTS 3,614,232 A  * 10/1971  Mathisen .................... 356/71
6,438,438 B1    8/2002  Takagi et al.
(Continued)

FOREIGN PATENT DOCUMENTS

JP    5-223751    8/1993
JP    7-201946    8/1995
(Continued)

OTHER PUBLICATIONS

Office Action in corresponding Japanese Application No. 2010-142177, mailed Jan. 14, 2014, with partial English translation.

*Primary Examiner* — Sath V Perungavoor
*Assistant Examiner* — Janese Duley
(74) *Attorney, Agent, or Firm* — Baker Botts L.L.P.

(57) ABSTRACT

Disclosed is a defect inspection device that has an illumination optical system; a detection optical system; and a processing unit which includes a defect feature quantity calculation unit that calculates the feature quantities of each defect candidate, a defect candidate grouping unit that groups the aforementioned defect candidates on the basis of the feature quantities, a defect classification evaluation value calculation unit that calculates defect classification evaluation values for the aforementioned defect candidates, a defect classification evaluation value updating unit that, on the basis of instructions, updates the evaluation values, a defect classification threshold determination unit that, on the basis of evaluation valued updated by the aforementioned defect classification evaluation value updating unit, determines a classification boundary that is a threshold for classifying defect types of the aforementioned defect candidates, and a defect detection unit that detects defects using the thresholds.

20 Claims, 26 Drawing Sheets

(51) Int. Cl.
    *G06T 7/00*      (2006.01)
    *G01N 21/956*    (2006.01)
    *G01N 21/88*         (2006.01)
    *H01L 21/66*         (2006.01)

(52) U.S. Cl.
    CPC ..... *G06T 7/0004* (2013.01); *G06T 2207/10061* (2013.01); *G06T 2207/30121* (2013.01); *G06T 2207/30148* (2013.01); *H01L 22/12* (2013.01); *G01N 21/95607* (2013.01)

(56) References Cited

U.S. PATENT DOCUMENTS

| | | | |
|---|---|---|---|
| 2002/0168787 A1 | 11/2002 | Noguchi et al. | |
| 2004/0188609 A1* | 9/2004 | Miyai et al. | 250/310 |
| 2004/0218806 A1 | 11/2004 | Miyamoto et al. | |
| 2004/0234120 A1 | 11/2004 | Honda et al. | |
| 2006/0078189 A1* | 4/2006 | Hosoya et al. | 382/149 |
| 2006/0082763 A1 | 4/2006 | Teh et al. | |
| 2008/0292176 A1* | 11/2008 | Sakai et al. | 382/144 |
| 2008/0317329 A1 | 12/2008 | Shibuya et al. | |
| 2009/0010527 A1 | 1/2009 | Honda et al. | |
| 2009/0045338 A1 | 2/2009 | Miyai et al. | |

FOREIGN PATENT DOCUMENTS

| | | |
|---|---|---|
| JP | 11-344450 | 12/1999 |
| JP | 2001-188906 | 7/2001 |
| JP | 2002-090312 | 3/2002 |
| JP | 2004-47939 | 2/2004 |
| JP | 2004-77164 | 3/2004 |
| JP | 2004-79593 | 3/2004 |
| JP | 2004-117130 | 4/2004 |
| JP | 3566589 | 6/2004 |
| JP | 2004-295879 | 10/2004 |
| JP | 2006-98155 | 4/2006 |
| JP | 2006-220644 | 8/2006 |
| JP | 4095860 | 3/2008 |
| JP | 2008-516259 | 5/2008 |
| JP | 2009-2743 | 1/2009 |
| JP | 2009-103508 | 5/2009 |
| WO | WO 2009/054102 A1 | 4/2009 |

* cited by examiner

FIG. 26
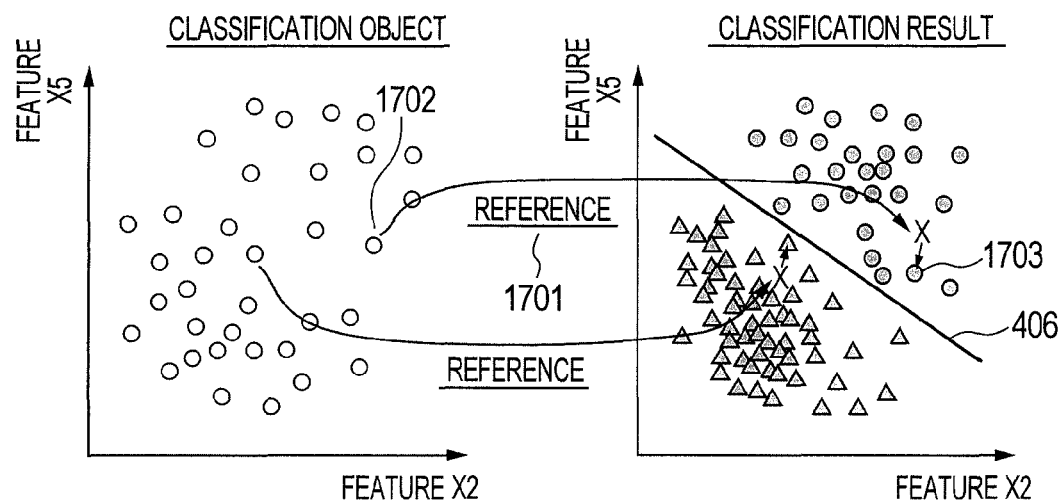
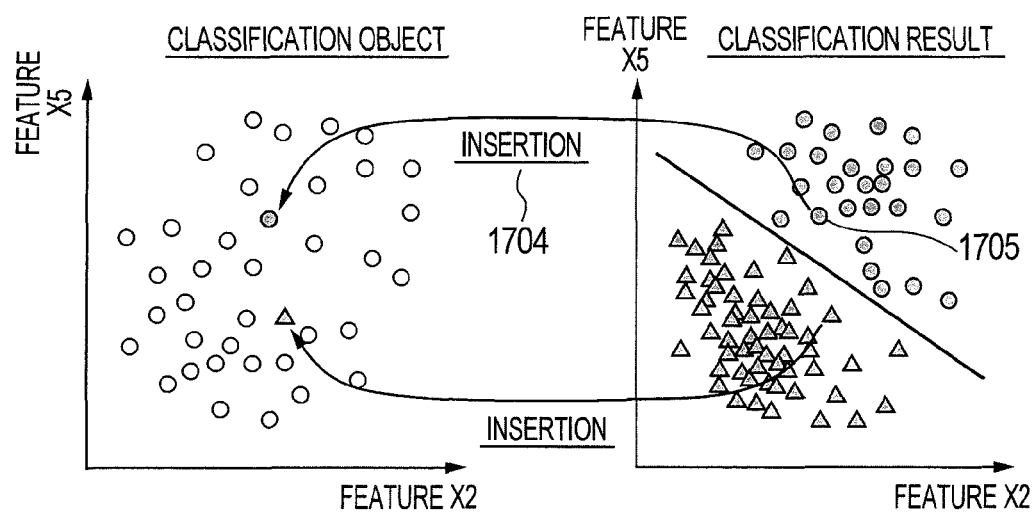

DEFECT INSPECTION DEVICE AND DEFECT INSPECTION METHOD

TECHNICAL FIELD

The present invention relates to a defect inspection device and defect inspection method for high-sensitivity inspection of microscopic defects present on a sample surface.

BACKGROUND ARTS

Thin-film devices such as semiconductor wafers or for use in liquid crystal displays and magnetic heads for hard disk drives are fabricated through a large number of processing steps. In the fabrication of such a thin-film device, an appearance inspection is performed at the end of each of process flows for the purpose of yield improvement and consistent production. In the appearance inspection, a pattern defect or a defect such as foreign substance is detected based on a reference image and an inspection image obtained by illuminating a region with lamp light, laser, electron beam or the like, the region corresponded by two patterns which are to be fundamentally formed in the same configuration. More specifically, the reference image and inspection image are registered with each other and a difference therebetween is calculated. The difference is compared with a previously defined threshold. A portion exhibiting a greater difference than the threshold is detected as a defect or foreign substance. Patent Literature 1 (Patent Publication No. 3566589) discloses the following defect inspection method as a threshold calculation method. The defect inspection method includes: an illumination step wherein longitudinally nearly parallel slit beams are applied onto a substrate as an inspection object which is formed with a circuit pattern and carried on a stage, the slit beams applied substantially at right angles to a scanning direction of the stage having a predetermined inclination relative to the normal direction of the substrate, having a plane inclined at a predetermined angle to a main straight line group of the circuit pattern and carrying thereon the substrate as the inspection object in a longitudinal direction; a detection step wherein reflective scattered light from a defect such as a foreign substance present on the substrate as the inspection object illuminated by the illumination step is received by an image sensor and converted into a signal for detection; and a defect judgment step wherein a signal indicative of the defect such as the foreign substance is extracted on the basis of the signal detected by the detection step.

In such an inspection, the detection of microscopic defects requires defect judgment to be made with a threshold set to a low value. However, the judgment with the low threshold entails the detection of a large number of false defects attributable to sampling errors, microscopic pattern differences such as roughness and grains, luminance variations due to film thickness variations or the like. If the threshold is set to such a high value as to sufficiently lower the rate of false defects to the entire wafer, the sensitivity is traded off, disabling the detection of microscopic defects. A method for enhancing the sensitivity is disclosed in Patent Literature 2 (JP-A No. 2004-79593). The method includes the steps of: performing a preliminary inspection for obtaining locations of the false defects; dividing an inspection region into a plurality of areas according to the densities of false defects; and applying a different threshold to each of the divided areas and determining the presence of the foreign substance on the surface of the inspection object on the basis of intensity of detected reflection light or scattered light. Further, Patent Literature 3 (JP-A NO. 2009-2743) discloses an appearance inspection method for defect detection by the use of detection signal obtained by applying light or electron beam onto a substrate to be inspected. This appearance inspection method includes: a step of calculating a feature quantity on the basis of an image of the detected defect; a step of calculating a coordinate feature quantity on the basis of positional information on the detected defect; and a step of outputting real defect information by performing false defect judgment according to a decision tree defined by a threshold processing on one of the image feature quantity and the image feature quantity. Furthermore, Patent Literature 4 (Patent Publication No. 4095860) discloses an inspection method for sample defect. The method includes: a step of capturing an appearance image of an observation object; a step of detecting an area of the appearance image that is different from an expected appearance; a step of calculating a feature quantity of the detected area; a step of superimposing on top of each other images containing the areas different from the expected appearance that are detected by sequentially performing an operation flow from the image capturing step to the calculation step on a plurality of observation objects of the sample which should fundamentally have the same appearance, and grouping the areas containing defect candidates which are produced by nearby grains or film thickness interference and are in proximity but not necessarily the same; a step of summing up the feature quantities of the detected areas in each of the obtained groups; and a step of deciding an attribute of the detected area by comparing the feature quantity of the detected area belonging to the group with a distribution of the feature quantity sums. Furthermore, Patent Literature 5 (JP-A No. 2006-98155) discloses an inspection method which includes the steps of: inspecting a sample; displaying on a screen an image of defects detected in the inspection; specifying a target defect selected from the displayed defects; extracting, from the image of the detected defects, a defect having a feature quantity similar to that of the specified target defect; displaying an image of the extracted defect on the screen; instructing a defect present in the displayed defect image and similar to the specified target defect; defining a defect inspection condition based on the instruction-input information; and inspecting the sample based on the defined inspection condition.

CITATION LIST

Patent Literatures

Patent Literature 1: Japanese Patent Publication No. 3566589
Patent Literature 2: JP-A No. 2004-79593
Patent Literature 3: JP-A No. 2009-2743
Patent Literature 4: Japanese Patent Publication No. 4095860
Patent Literature 5: JP-A No. 2006-98155

SUMMARY OF INVENTION

Technical Problem

In the semiconductor wafer as the inspection object, even adjoining chips have a sensitive difference in film thickness which results from CMP planarization or the like. Hence, an image shows a local luminance difference between chips. There are also known other causes for producing luminance variations which are different from area to area, the causes including grains (micron-scaled protrusions and recesses on surface), line edge roughness (LER) and the like.

If a detection image is compared with a reference chip image in terms of luminance and a portion exhibiting a difference greater than a certain threshold 'th' is determined to be a defect according to the conventional method, an area determined, by the image comparison, to have a great luminance difference due to the film thickness variations or pattern edge variations is also detected as the defect. However, this area should not fundamentally be detected as the defect. Namely, this area is a false defect. It has been a conventional practice to set the defect detection threshold 'th' to a higher value in order to obviate the detection of the false defect. This approach, however, entails the decrease in sensitivity, failing to detect a defect exhibiting a difference equal to or less than the threshold.

As LSI patterns become more miniaturized and complicated, whether the defect affects the yield or not cannot be determined on the basis of a single definition. Hence, a user is required to make flexible defect judgment on a case-by-case basis. The user is allowed to classify defects into a defect which is not desired by the user to be detected (hereinafter, referred to as "Nuisance") and a defect which is desired by the user to be detected (DOI). It is therefore an object of the invention to provide a defect inspection device and defect inspection method that provide feasible classification of defect candidates for the purpose of reducing the above noises and Nuisances increased with increase in the number of types of defects detected at high sensitivity and in the inspection sensitivity, as well as for the sake of accomplishing the extraction of DOI.

In a case where the above-described classification of defect candidates is performed, however, means is necessary for permitting the user to indicate his intension by, for example, giving an instruction. In the light of process time and burden on the user, it is not practicable for the user to check the defect candidates one by one and to give an instruction accordingly. In contrast, if the instruction is given to only some of the defects, the defects may not be correctly classified into 'DOI' or 'Nuisance', resulting in lowered classification accuracy.

In this connection, the invention solves the above problems of the conventional inspection technique and discloses method of carrying out a defect inspection technique for reducing the detection of false defects due to the luminance variations between the compared images and for accomplishing high-sensitivity, high-speed extraction of the DOI desired by the user in the defect inspection wherein images of regions corresponded by two patterns which are to be fundamentally formed in the same configuration are compared and a portion of one image that does not match with a corresponding portion of the other image is determined to be a defect. The luminance variations between the compared images are caused by sensitive film thickness differences, grains or the like.

Solution to Problem

Typical features of the invention disclosed by this application are briefly described as follows.
(1) A defect inspection device includes: an illumination optical system for illuminating a sample with light; and a detection optical system for detecting scattered light from the sample illuminated by the illumination optical system, the device further including: a defect feature quantity calculation unit that calculates a feature quantity of each defect candidate extracted on the basis of the scattered light detected by the detection optical system; a defect candidate grouping unit that performs grouping of the defect candidates on the basis of the feature quantity calculated by the defect feature quantity calculation unit; a defect classification evaluation value calculation unit that calculates a defect classification evaluation value of the defect candidate on the basis of the feature quantity calculated by the defect feature quantity calculation unit; a defect classification evaluation value updating unit that updates, on the basis of an instruction, the evaluation value calculated by the defect classification evaluation value calculation unit; a defect classification threshold determination unit that determines, on the basis of the evaluation value updated by the defect classification evaluation value updating unit, a classification boundary as a threshold for classification of the defect candidates into defect types; and a defect detection unit that detects a defect using the threshold determined by the defect classification threshold determination unit.

Advantageous Effect of Invention

The invention disclosed in the present application provides the defect inspection device and defect inspection method that are capable of high-sensitivity inspection of microscopic defects present on the surface of the sample.

BRIEF DESCRIPTION OF DRAWINGS

FIG. 26 is a group of diagrams for explaining a method wherein classified defects are used for instructional purpose.

DESCRIPTION OF EMBODIMENTS

Figure 1:
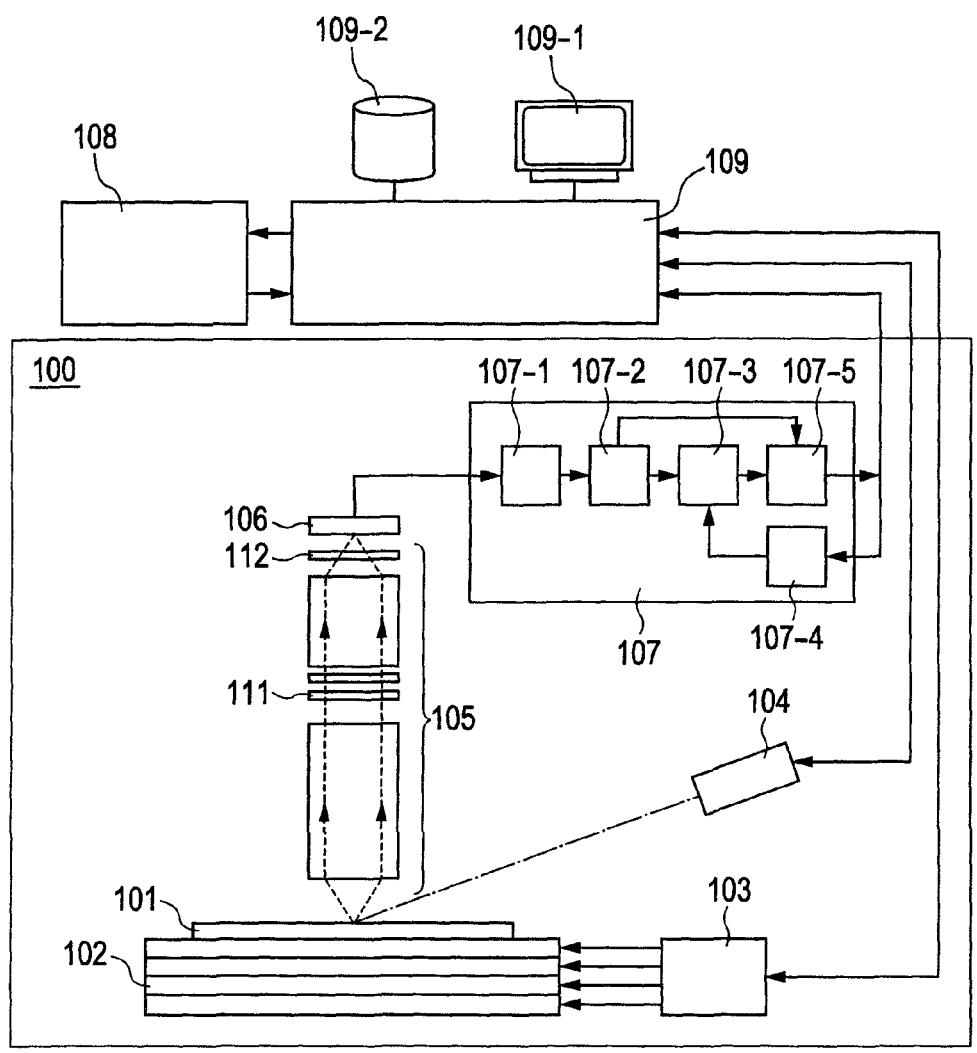
FIG. 1 is a diagram showing an exemplary arrangement of a defect inspection device according to a first embodiment of the invention.

The preferred embodiments of the invention will be hereinbelow described in detail with reference to the accompanying drawings. In all the drawings for illustrating the embodiments hereof, the same or similar reference numerals are essentially used to refer to the same or similar components which are explained only once to avoid repetition.

First Embodiment

A defect inspection technique (defect inspection method and defect inspection device) according to a first embodiment of the invention will be described in detail as below.

A pattern inspection technique according to the first embodiment of the invention is described by way of example of a defect inspection device and defect inspection method using dark field illumination of a semiconductor wafer as an inspection object.

FIG. 1 shows an exemplary arrangement of a defect inspection device using dark field illumination according to the first embodiment. The defect inspection device of the first embodiment includes a defect detection unit 100, a post-inspection processing unit 108 and a main control unit 109 (including a user interface 109-1 and a recording unit 109-2).

The defect detection unit 100 includes a stage 102, a mechanical controller 103, an illumination optical system (illumination unit) 104, a detection optical system (upper detection system) 105, a spatial frequency filter 111, an analyzer 112, an image sensor 106, and an image comparison processing unit 107 (preprocessing unit 107-1, image memory 107-2, defect candidate detection unit 107-3, parameter setting unit 107-4, clipped image creation unit (patch image clipper) 107-5).

A sample 101 is an inspection object such as a semiconductor wafer. The stage 102 carries thereon the sample 101 and is capable of movement in XY plane, rotation (θ) and movement in Z direction. The mechanical controller 103 drives the stage 102. The illumination unit 104 illuminates the sample 101 with light, while the detection optical system (upper detection system) 105 focuses the scattered light from the sample 101 into an image. The focused image is received by each image sensor 106 to be converted into an image signal. In the meantime, the sample 101 is carried on the X-Y-Z-θstage 102 which is moved in a horizontal direction while scattered light from foreign particles on the sample is detected. A detection result is obtained as a two-dimensional image (a dark field image: a DF image).

The illumination unit 104 may employ laser or lamp as a light source thereof. The light of the illumination light source may be short wavelength light or light in a broad band of wavelengths (white light). In the case of using the short wavelength light, light having wavelength in ultraviolet range (Ultra Violet Light: UV light) may also be used for the sake of increasing the resolution of a detection image (detecting microscopic defects). In the case of using a laser as the light source, each illumination unit 104 may also be provided with means for reducing coherence (not shown) if the laser has a single wavelength.

A time delay integration image sensor (TDI image sensor) including a plurality of one-dimensional image sensors arranged in a two-dimensional configuration may be employed as the image sensor 106. In synchronous with the movement of the stage 102, each one of the one-dimensional image sensors detects and transfers a signal to the subsequent image sensor so as to add up the signals sequentially. This permits a two-dimensional image to be captured at relatively high speed and with relatively high sensitivity. The inspection device may employ, as the TDI image sensor, a parallel output sensor equipped with a plurality of output taps so as to provide for parallel processing of outputs from the sensors. Thus, the inspection device can achieve faster signal detection. If a backside illumination type sensor is employed as the image sensor 106, the inspection device can achieve higher detection efficiency than in a case where a front side illumination type sensor is employed.

The image comparison processing unit 107 for extracting a defect candidate in a wafer as the sample 101 includes: the preprocessing unit 107-1 for performing image correction including shading correction, black level correction and the like on the detected image signal; the image memory 107-2 for storing a digital signal representing the corrected image; the defect candidate detection unit 107-3 for extracting the defect candidate by comparison of images representing corresponding areas and stored in the image memory 107-2; the parameter setting unit 107-4 for setting processing parameters; and the clipped image creation unit 107-5 for clipping an image (clipped image, patch image) from a sub-area containing the detected defect candidate.

First, the preprocessing unit 107-1 performs the image corrections including the shading correction, black level correction and the like on the image signal and divides the image into image pieces of a given unit size to store them in the image memory 107-2. Retrieved from the image memory 107-2 are a digital signal representing an image of an inspected area (hereinafter, referred to as "detection image") and a digital signal representing an image of a corresponding area (hereinafter, referred to as "reference image"). The defect candidate detection unit 107-3 calculates a positional correction quantity for aligning the retrieved detection image and the reference image. The detection image and the reference image are aligned with each other by using the calculated positional correction quantity and a pixel having a feature quantity which is outlier value from features of corresponding pixel in a feature space is extracted. Such a pixel is outputted as the defect candidate. The parameter setting unit 107-4 sets inspection parameters including types of feature quantities, threshold values and the like which are externally inputted and used for extracting the defect candidate. The parameter setting unit 107-4 supplies the set inspection parameters to the defect candidate detection unit 107-3.

The main control unit 109 includes a CPU (incorporated in the main control unit 109), and is connected to the user interface 109-1 which includes input means for receiving, from a user, change in the inspection parameter (type of feature quantity, threshold and etc.) and display means for displaying information on the detected defect, and to the recording unit 109-2 for storing the feature quantities, the images and the like of the detected defect candidates. The mechanical controller 103 drives the stage 102 based on a control command sent from the main control unit 109. Further, the image comparison processing unit 107, the optical systems including the illumination unit 104 and the detection optical system 105 and the like are also driven by control commands from the main control unit 109.

The post-inspection processing unit 108 retrieves information on the defect candidate from the recording unit 109-2 and makes DOI/Nuisance judgment again on the defect candidate, and output a result of the judgment to the main control unit 109.

Figure 2:
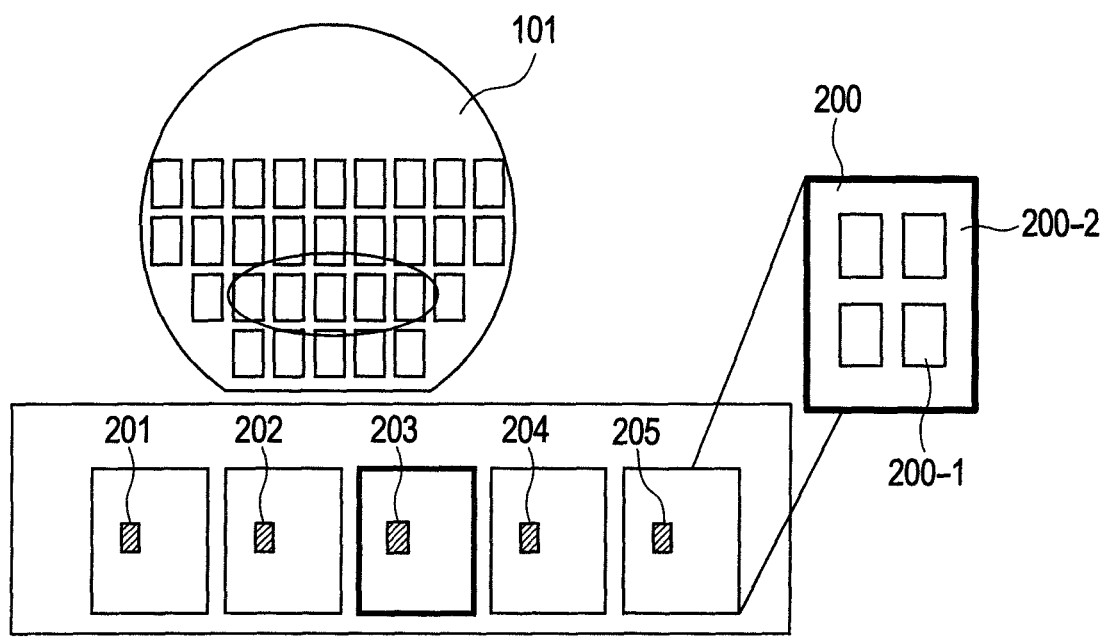
FIG. 2 is a diagram showing an exemplary arrangement of chips in the defect inspection device according to the first embodiment of the invention.

FIG. 2 is a diagram showing an exemplary arrangement of chips in the defect inspection device according to the first embodiment of the invention. The detection of the defect candidate by the defect candidate detection unit 100 is described as follows. The sample 101 (also described as "semiconductor wafer" or "wafer") as the inspection object includes a large number of chips 200 of the same pattern which are regularly arranged and each include a memory mat 200-1 and a peripheral circuit 200-2. The main control unit 109 continuously moves the stage 102 on which the semiconductor wafer 101 as the sample is mounted. In synchronism with the movement of the stage 102, the main control unit sequentially captures chip images through the image sensor 106. The main control unit 109 compares the detection image with reference images representing the corresponding areas of the regularly arranged chips. For example, digital image signals representing areas 201, 202, 204, 205 are defined as the reference images in correspondence to an area 203 of the detection image shown in FIG. 2. Namely, a pixel in the area 203 of the detection image is compared with the corresponding pixel in the area 201, 202, 204, 205 or with another pixel in the detection image. A pixel having a significant difference from the corresponding pixel is detected as the defect candidate.

Figure 3:
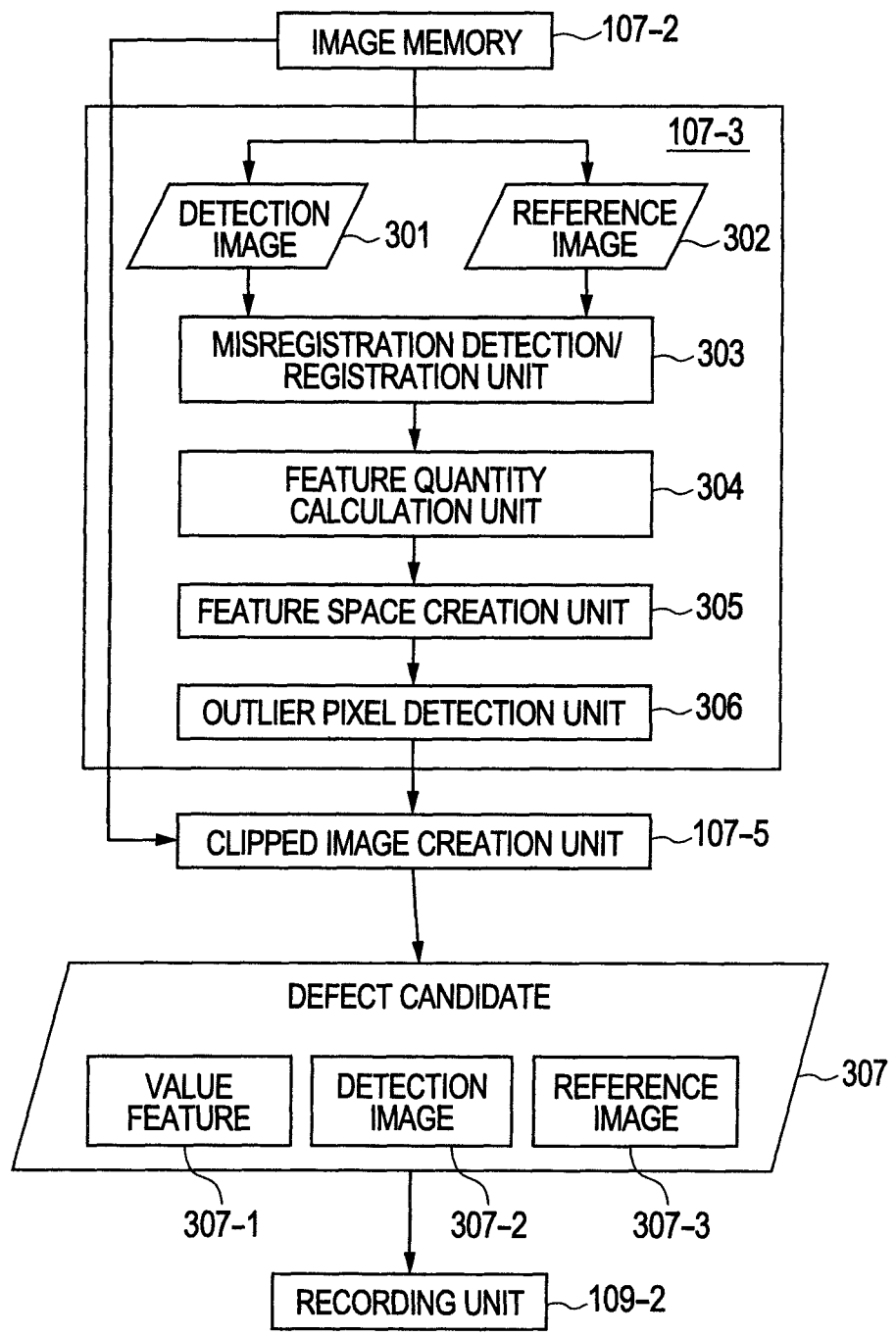
FIG. 3 is a diagram showing an exemplary operation flow of defect candidate extraction by the defect inspection device according to the first embodiment of the invention.

FIG. 3 is a diagram showing an exemplary operation flow of defect candidate extraction by the defect inspection device according to the first embodiment of the invention. The figure shows an exemplary flow of the operation which the defect candidate detection unit 107-3 performs on the image of the chip (area 203) as the inspection object shown in FIG. 2. First, an image of the chip as the inspection object (detection image 301) and a corresponding reference image 302 (an image of an adjoining chip 202 shown in FIG. 2, for example) are retrieved from the image memory 107-2. A misalignment detection/alignment unit 303 detects misalignment before registering the retrieved images (303). Next, a feature quantity calculation unit 304 obtains plural feature quantities by calculating differences between respective ones of the pixels of the registered detection image 301 and the respective ones of the corresponding pixels of the reference image 302 (304). The feature quantity may be any value that represents the feature of the pixel. Examples of the feature quantity include (1) luminance, (2) contrast, (3) brightness difference, (4) luminance variance of neighboring pixels, (5) correlation coefficient, (6) increase or decrease in luminance from that of neighboring pixel, (7) secondary differentiation value, (8) luminance variance and the like.

A feature space creation unit 305 creates the feature space by plotting the individual pixels in space having axes representing some or all of these feature quantities (305). A pixel plotted on the outside of data distribution in this feature space or a pixel representing a characteristic outlier value is detected as the defect candidate by an outlier pixel detection unit (306).

The clipped image creation unit 107-5 clips a sub-area around the defect candidate detected by the defect candidate detection unit 107-3 from each of the detection image and reference image stored in the image memory 107-2. The clipped images (patch images) obtained from a detection image 307-2 and a reference image 307-3 and a feature quantity (value features) 307-1 of a defect candidate calculated by the feature quantity calculation unit 304 are collectively defined as a defect candidate 307 which is stored in the recording device (recording unit) 109-2.

Figure 4:
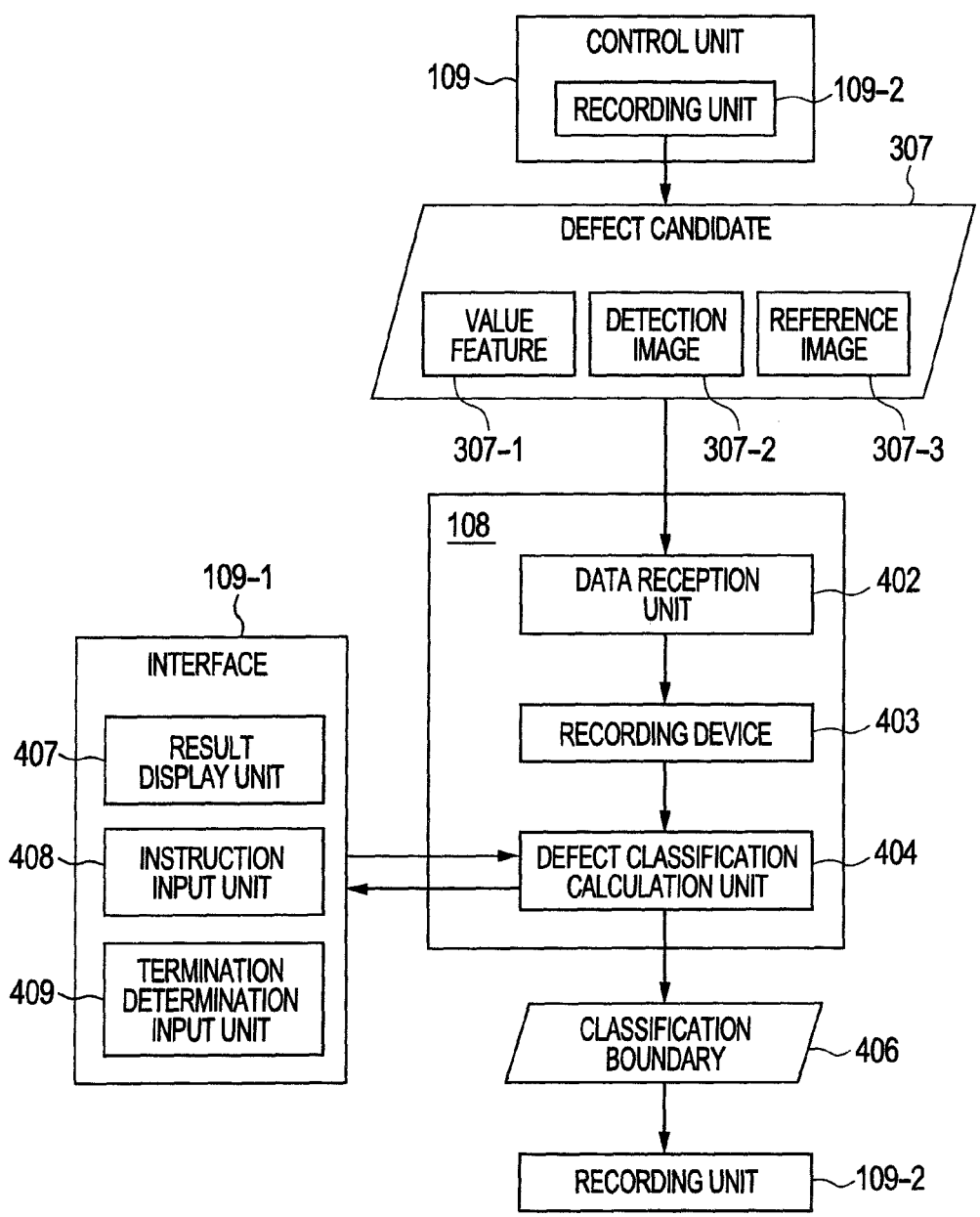
FIG. 4 is a diagram showing an exemplary arrangement of a post-inspection processing unit of the defect inspection device according to the first embodiment of the invention.

FIG. 4 is a diagram showing an exemplary arrangement of the post-inspection processing unit of the defect inspection device according to the first embodiment of the invention. The post-inspection processing unit 108 includes a data reception unit 402, a recording device (data recording device) 403 and a defect classification calculation unit 404.

The main control unit 109 transmits the defect candidate 307 (defect value feature 107-1, clipped image (patch image) 307-2 from the detection image, and clipped image 307-3 from the reference image) stored in the recording unit (recording device) 109-2 to the data reception unit 402 of the post-inspection processing unit 108. The post-inspection processing unit 108 transfers the defect candidate 307 from the data reception unit 402 to the recording device 403 in the post-inspection processing unit 108.

The defect classification calculation unit 404 retrieves the defect candidate 307 from the recording device 403 and classifies the defect candidate into a defect of importance (DOI) or a defect of no importance (Nuisance). The defect classification calculation unit 404 provides sequential display of a process of the classification on a result display unit 407 of the interface 109-1, enabling the user to view the process. The user checks the classification result displayed on the result display unit 407. If the displayed classification result is not what the user desires, the user manipulates an instruction input unit 408 to instruct that the defect candidate 307 is DOI or Nuisance. The display of the result and the user-input instruction are repeated till the user obtains the desired classification result. At the time when the user obtains the desired classification result, the user inputs "End" to a termination determination input unit 409. A classification boundary 406 as the result of the processing by the post-inspection processing unit 108 represents a classification boundary between DOI and Nuisance for each of the defect candidates. The classification boundary 406 may also be used as a label DOI or Nuisance. Outputting the classification boundary 406, the post-inspection processing unit 108 stores the resultant defect label and classification boundary 406 in the recording unit (recording device) 109-2 as a part of the control device (main control unit) 109. It is noted, however, that in a case where the recording unit (recording device) 109-2 directly inputs the image data to the post-inspection processing unit 108, the control device 109 may not include the recording device 403.

Figure 16:
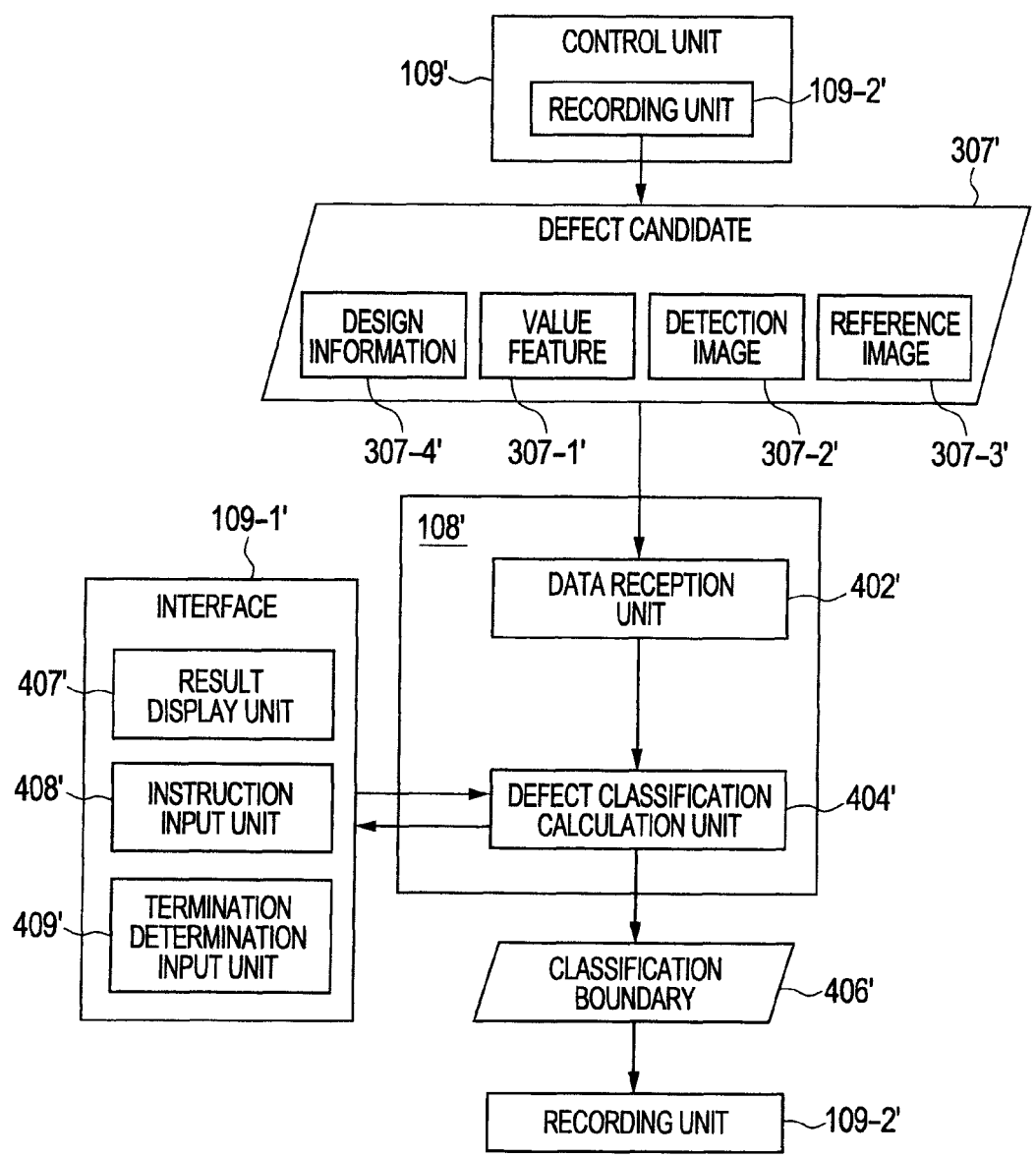
FIG. 16 is a diagram showing an exemplary modification of the arrangement of the post-inspection processing unit of the defect inspection device according to the first embodiment of the invention shown in FIG. 4.

FIG. 16 shows an exemplary modification of the arrangement of the post-inspection processing unit of the defect inspection device according to the first embodiment of the invention shown in FIG. 4.

The defect candidate 307 further includes design information 307-4'. The post-inspection processing unit 108 transmits the defect candidate from a data reception unit 402' directly to a defect classification calculation unit 404, skipping the recording device.

The defect classification calculation unit 404' classifies the defect candidate 307' including the design information 307-4' on the sample 101 into the defect of importance (DOI) or the defect of no importance (Nuisance) and provides the sequential display of the classification process on a result display unit 407' of an interface 109-1', enabling the user to view the process. The user checks the classification result displayed on the result display unit 407'. If the displayed classification result is not what the user desires, the user manipulates an instruction input unit 408' to input the user's instruction to the defect classification calculation unit 404'. The defect classification calculation unit 404' performs the defect classification again on the basis of the user's instruction.

The display of the result and the user's instruction are repeated till the user obtains the desired classification result. At the time when the user obtains the desired classification result, the user inputs "End" to the defect classification calculation unit via a termination determination input unit 409'. The defect classification calculation unit 404' receives an end command from the user and stores a classification boundary 406' in a recording unit (recording device) 109-2' as a part of a control unit (main control unit) 109'.

Figure 5:
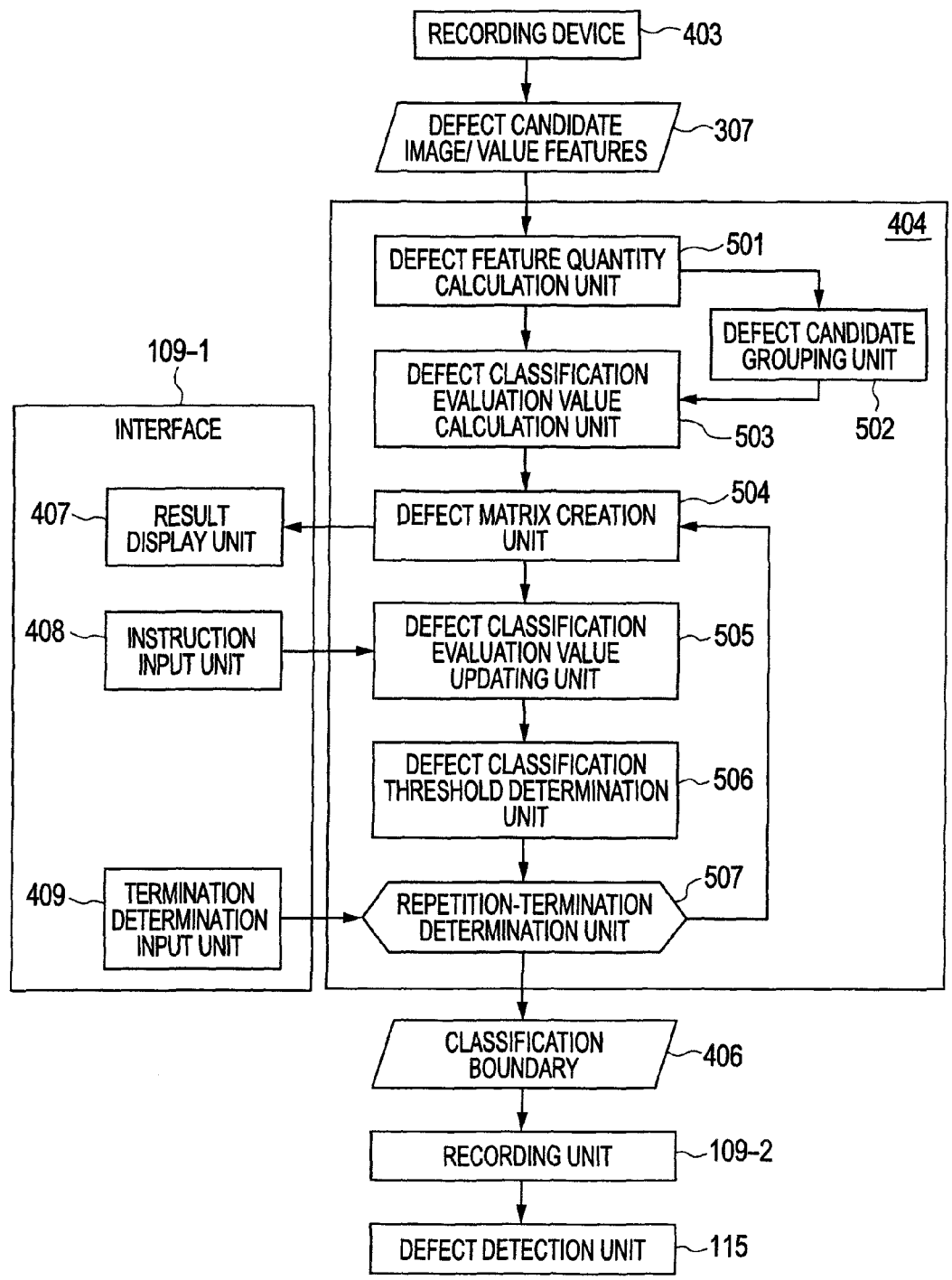
FIG. 5 is a diagram showing an exemplary arrangement of a defect classification calculation unit of the defect inspection device according to the first embodiment of the invention.

FIG. 5 is a diagram showing an exemplary arrangement of the defect classification calculation unit of the defect inspection device according to the first embodiment of the invention. The defect classification calculation unit 404 receives the defect candidate 307 from the recording device 403. A defect feature quantity calculation unit 501 calculates a feature quantity from the defect candidate 307. On the basis of the feature quantity calculated by the defect feature quantity calculation unit 501, a defect candidate grouping unit 502 classifies the defect candidate 307 into a similar-defect group. Grouping criteria include (1) similarity of the reference images (background image), (2) proximity between the defect candidates, (3) configuration similarity of the defect candidates and the like. As the feature quantity used by the defect candidate grouping unit 502, the defect feature quantity calculation unit 501 calculates, from the detection image 307-2, reference image 307-3 and value feature 307-1 of the defect candidate 307, (1) luminance, (2) contrast, (3) brightness difference, (4) luminance variance of neighboring pixels, (5) correlation coefficient, (6) increase or decrease in luminance from that of neighboring pixel, (7) secondary differentiation value or the like. As a grouping method, the defect candidate grouping unit 502 uses a generally used pattern classification method such as classification according to decision tree, classification using support vector machine and classification based on nearest neighbor rule.

Next, a defect classification evaluation value calculation unit 503 receives the feature quantity from the defect feature quantity calculation unit 501 and calculates an evaluation value for evaluating the defect importance (DOI) of the defect candidate. The defect classification evaluation value calculation unit 503 selects a feature quantity for calculation of the evaluation value from the feature quantities calculated by the defect feature quantity calculation unit 501, which include: (1) luminance, (2) contrast, (3) brightness difference, (4) luminance variance of neighboring pixels, (5) correlation coefficient, (6) increase or decrease in luminance from that of neighboring pixel, (7) secondary differentiation value and the like of an image of an area around the defect candidate. The defect classification evaluation value calculation unit 503 calculates a defect classification evaluation value 'g' using the selected feature quantity. The unit calculates the value 'g' as follows. Provided that x1, x2, x3 represent respective feature quantities, for example, the defect classification evaluation value 'g' can be expressed as g=i(x1,x2,x3), where 'i' denotes the feature quantity integration function. The defect classification evaluation value can be expressed in a linear or non-linear polynomial or the like. Provided that w1, w2, w3 represent respective weights, for example, a weighted linear sum can be defined as i(x1,x2,x3)=w1·x1+w2·x2+w3·x3.

Next, a defect matrix creation unit 504 creates a defect matrix on the basis of the group determined by the defect candidate grouping unit 502 and the per-group defect classification evaluation value determined by the defect classification evaluation value calculation unit 503. The defect matrix shows the defect candidates by plotting the group determined by the defect candidate grouping unit 502 on the abscissa and the defect classification evaluation value determined by the defect classification evaluation value calculation unit 503 on the ordinate. The defect matrix creation unit 504 transmits the resultant defect matrix to the result display unit 407 of the user interface 109-1. The result display unit 407 displays the defect matrix to the user. The user checks the defect matrix displayed by the result display unit 407 and gives an instruction 'DOI' or 'Nuisance' on the defect candidate via the instruction input unit 408.

A defect classification evaluation value updating unit 505 updates the defect classification evaluation value on the basis of the user's instruction sent from the instruction input unit 408 and the defect matrix inputted by the defect matrix creation unit 504. The updating of the defect classification evaluation value, which will be described in detail hereinafter, is equivalent to rearrangement of the defect candidates arranged in the order of defect classification evaluation value.

A defect classification threshold determination unit 506 determines the classification boundary 406, based on which the defect candidate is classified into 'DOI' or 'Nuisance', on the basis of the defect candidates rearranged by the defect classification evaluation value updating unit. A repetition-termination determination unit 507 displays to the user the defect matrix and the classification boundary 406. If a desired DOI is correctly extracted, the user decides to terminate the classification and takes a step to terminate the classification via the termination determination input unit 409. If the user does not decide to terminate the classification, the defect matrix creation unit 504 displays to the user a defect matrix again so that the user enters an instruction again via the instruction input unit 408. The user repeats these steps in cycles till the DOI desired by the user is extracted. When the user inputs "End" to the termination determination input unit 409, the repetition-termination determination unit 507 outputs to the recording unit (recording device) 109-2 a classification boundary 406 defined at the time of repetition termination. A defect detection unit 115 detects a defect using the classification boundary 406 thus defined.

Figure 17:
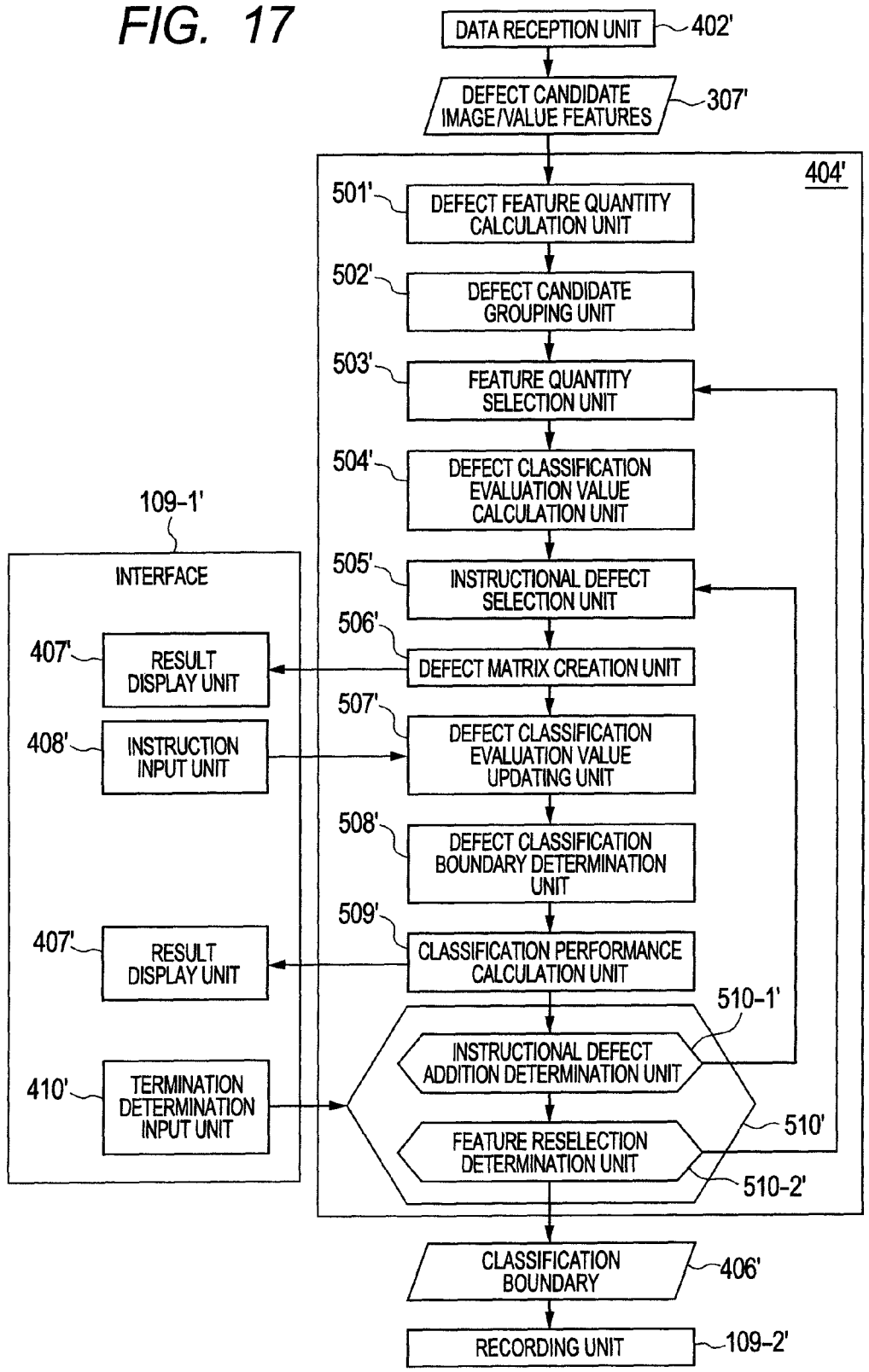
FIG. 17 is a diagram showing an exemplary modification of the arrangement of the defect classification calculation unit of the defect inspection device according to the first embodiment of the invention shown in FIG. 5.

FIG. 17 shows an exemplary modification of the arrangement of the defect classification calculation unit of the defect inspection device according to the first embodiment of the invention shown in FIG. 5.

The recording device 403 of FIG. 5 is replaced by the data reception unit 402' while the defect classification calculation unit 404' includes some additional steps. Further, the interface 109-1 includes an additional result display unit 407' for displaying a result supplied by a classification performance calculation unit 509'.

In FIG. 17, the defect classification calculation unit 404' receives the defect candidate 307' from the data reception unit 402'. The defect feature quantity calculation unit 501' in the defect classification calculation unit 404' calculates a feature quantity from the defect candidate 307'. The feature quantity calculated by the defect feature quantity calculation unit 501' may be one selected from the group of: (1) luminance, (2) contrast, (3) brightness difference, (4) luminance variance of neighboring pixels, (5) correlation coefficient, (6) increase or decrease in luminance from that of neighboring pixel, (7) secondary differentiation value and the like, which are obtained from the detection image 307-2, the reference image 307-3 and the value feature 307-1 of the defect candidate 307'. Further, any one selected from the group of: (8) distribution density about each defect candidate, (9) distance to the nearest defect candidate, (10) distance from the centroid of distribution and the like in the feature space defined by the above feature quantities may also be used as one of the feature quantities. Furthermore, (11) pattern proximity based on design information may also be used as one of the feature quantities. The defect candidate grouping unit 502 groups the defect candidate 307' into a similar-defect group on the basis of the feature quantity calculated by the defect feature quantity calculation unit 501'. The grouping criteria include: (1) similarity of the reference images (background), (2) proximity between the defect candidates, (3) configuration similarity of the defect candidates, (4) crude density of design pattern and the like.

A feature quantity selection unit 503' selects at least one feature quantity from the feature quantities calculated by the defect feature quantity calculation unit 501' so as to create the feature space. Since the feature quantity effective for the classification varies for each type of DOI which the user desires to be extracted, the feature quantity is selected on the basis of the user-input instruction. The feature quantity may be selected by any methods. For example, a feature quantity that permits defects to be most accurately classified on the basis of the user's instruction may be selected. Alternatively, the feature quantity may be selected by discrimination analysis or the like. Otherwise, the user may select any feature quantity at will. In an initial stage when the user's instruction is not given yet, a previously defined feature quantity or a feature quantity applied to the previous classification may be used.

Subsequently, the defect classification evaluation value calculation unit 504' receives the feature quantity selected by the defect feature quantity selection unit 503' and calculates a defect classification evaluation value 'g' for the evaluation of the importance DOI of the defect candidate. Provided that x1, x2, x3 represent the selected feature quantities respectively, for example, the defect classification evaluation value 'g' can be expressed as $g=i(x1,x2,x3)$.

Next, an instructional defect selection unit 505' selects from the defect candidate 307' a defect to be used by the user to give the instruction. Any method may be used for selecting the defect from the defect candidate. For example, the defect may be selected at random from the all defect candidates per group. Alternatively, the defect may be automatically selected from the proximity of the classification boundary which is the result outputted from a defect classification boundary determination unit 508'. Otherwise, the user may select the defect at will.

In a case where the instructional defect is selected from the proximity of the classification boundary, however, it is impossible to select the instructional defect by utilizing the classification boundary in the initial stage when the classification boundary is not calculated yet. Hence, a rough classification may be first performed by principal component analysis, k-means clustering method or the like and thereafter, the classification boundary thus obtained may be used for selecting the instructional defect. It is also possible to select an instructional image by using a classification boundary obtained by the previous boundary classification. The selection of the defect candidate leads to the reduction of the number of defect candidates which the user compares for giving the instruction. Hence, the burden on the user and instruction time can be reduced while enhanced instruction correctness can be achieved. Thus is provided user friendly DOI/Nuisance classification.

Next, the defect matrix creation unit 506 displays a matrix of the defect candidates selected by the instructional defect selection unit 505'. In the matrix, the group determined by the defect candidate grouping unit 502' is plotted on the abscissa and the defect classification evaluation value determined by the defect classification evaluation value calculation unit 504 is plotted on the ordinate.

When the user inputs the instruction to the instruction input unit 408' to classify the defect candidate into 'DOI' or 'Nuisance', the user may make judgment by visually inspecting not only the image of the defect candidate but also optical microscope image or scanning electron microscope image thereof. If, at this time, the instruction is given based on information on other than an inputted defect candidate 307', the inputted defect candidate is regarded as a fuzzy defect unclassifiable just by the defect candidate information and thence, may be weighted by the defect classification calculation unit 404' to reduce influence on the classification. This approach is adopted, for example, in a case where an input to the post-inspection processing unit 108 includes only a dark field image and hence, the instruction is given based on an optical microscope image. Further, the defect candidate in question can be deleted in order to eliminate the influence thereof.

The defect classification evaluation value updating unit 507' updates the defect classification evaluation value on the basis of the user's instruction supplied from the instruction input unit 408'.

The defect classification boundary determination unit 508' determines the classification boundary 406', based on which the defect candidate is classified into 'DOI' or 'Nuisance', on the basis of the defect candidates rearranged by the defect classification evaluation value updating unit 507'. A generally used classification method may be used for determining the classification boundary 406'. Examples of the usable classification method include: classification according to decision tree, classification using support vector machine, classification based on nearest neighbor rule and the like. In this process, a different classification boundary may be defined for each group or a uniform classification boundary may be shared among the individual groups. It is also possible for the user to directly specify or change the classification boundary by inputting an instruction to the instruction input unit 408'. The user repeats the sequence of operations on the defect classification evaluation value updating unit 507' in multiple cycles with the use of the matrix result display unit 407' and the instruction input unit 408'. Thus, the user can achieve flexible DOI/Nuisance classification by using the judgment criteria which vary from user to user.

The classification performance calculation unit 509' calculates a classification accuracy rate of the instruction-defined defects and a quantity of estimation performance progress caused by adding the instructional defect on the basis of the instruction-defined defect and the classification boundary 406' determined by the defect classification boundary determination unit 508'. The result display unit 407' displays, to the user, the quantity of performance progress and the classification accuracy rate thus calculated.

Figure 18:
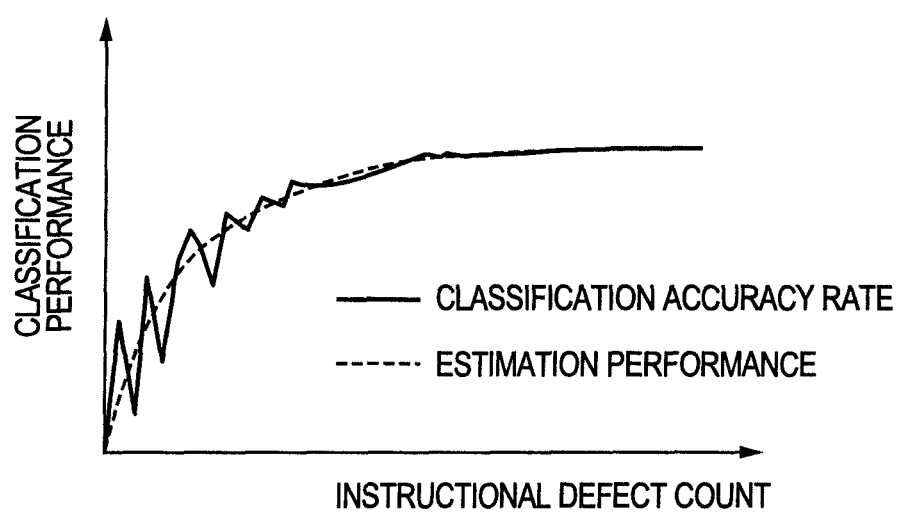
FIG. 18 is a graph showing a relation between the instructional defect count and the classification performance.

FIG. 18 is a graph showing a relation between the instructional defect count and the classification performance. As shown in FIG. 18, the relation between the instructional defect count and the classification performance is generally characterized in that the classification performance is improved with the increase in the instructional defect count but the performance improvement converges at a certain instructional defect count. The quantity of estimation performance progress can be determined from the fluctuation range of classification accuracy rate or the differential value of estimation performance. Alternatively, the quantity of estimation performance progress may also be determined by fitting an arbitrary polynomial to the classification accuracy and extrapolating a classification estimate value.

A repetition determination unit 510' shown in FIG. 17 includes an instructional defect addition determination unit 510-1' and a feature reselection determination unit 510-2'. The instructional image addition determination unit 510-1' receives the above-described information of classification accuracy rate and quantity of estimation performance progress from the classification performance calculation unit 509' and determines whether to add the instructional defect. If the classification performance is improved by adding the instructional defect, the steps subsequent to the instructional defect selection unit 505' are repeated. If the classification performance is not improved by adding the instructional defect, an operation of the feature reselection determination unit 510-2' is performed. The feature reselection determination unit 510-2' receives the classification accuracy rate from the classification performance calculation unit 509'. If the received classification accuracy rate is lower than a user preset value inputted to a termination determination input unit 410', the steps subsequent to the feature quantity selection unit 503' are repeated. If the classification accuracy rate is higher than the preset value, the repetition of the above steps is terminated. If the user checks the classification performance displayed by the result display unit 407' and determines that the desired DOI/Nuisance classification is accomplished, the user can terminate the repetition of the above steps by inputting a repetition end command to the termination determination input unit 410'. The classification boundary 406', the respective feature quantities of the defect candidates, the selected feature quantity, the result of the instruction to the selected defect candidate, the grouping criteria and the like as determined at the time of repetition termination are outputted to the recording unit (recording device) 109-2'.

Figure 6:
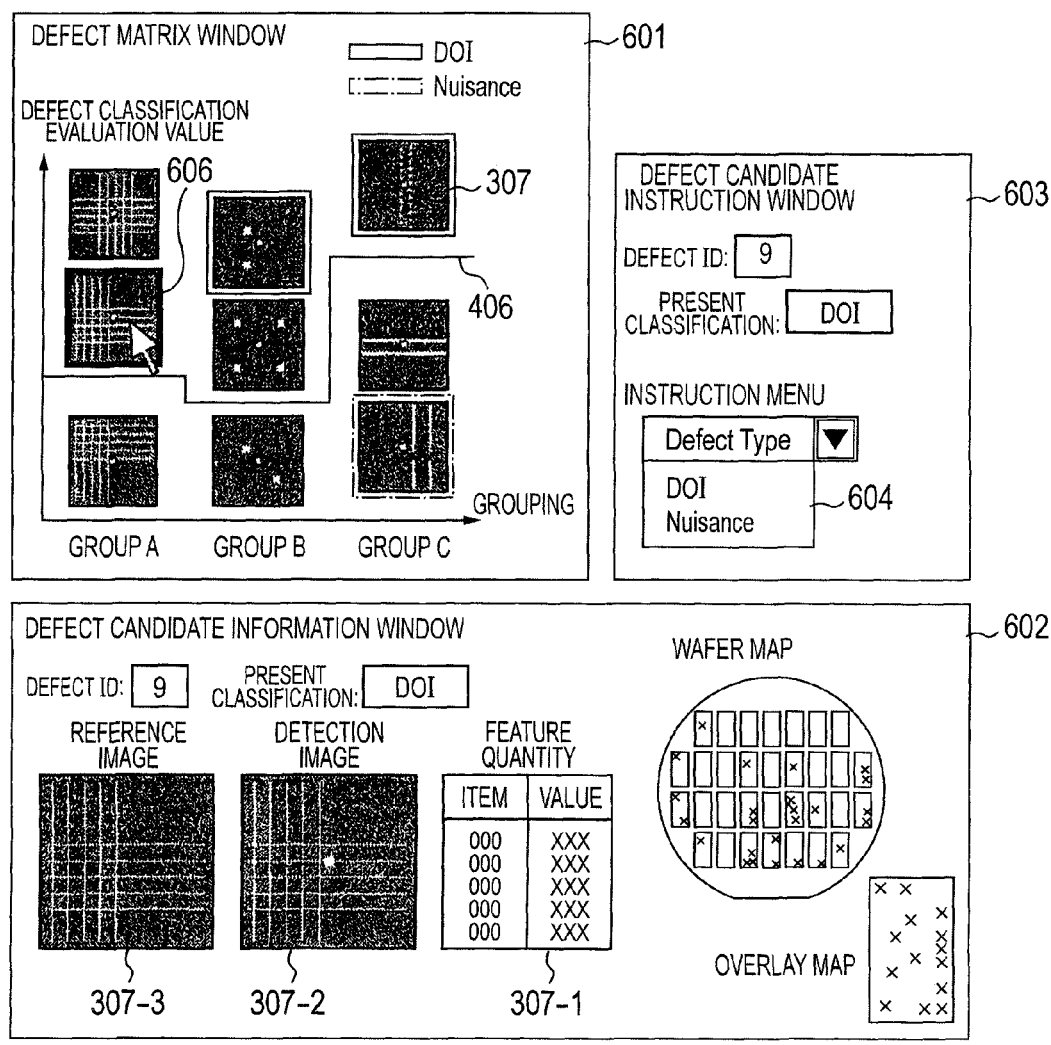
FIG. 6 is a diagram showing an exemplary defect candidate instructional GUI of the defect inspection device according to the first embodiment of the invention.

FIG. 6 is a diagram showing an exemplary defect candidate instructional GUI of the defect inspection device according to the invention. An exemplary display of the defect matrix created by the defect matrix creation unit 504 and an example of the user-input instruction are shown in FIG. 6. The defect matrix creation unit 504 displays the defect matrix in a defect matrix window (defect candidate window) 601 of the result display unit 407. The displayed defect matrix shows the defect candidates by plotting the group on the abscissa and the defect determination evaluation value on the ordinate. Furthermore, the defect matrix shows the classification boundary 406 between 'DOI' and 'Nuisance'. The user selects a defect candidate by means of an input device such as a mouse. In the example of FIG. 6, a defect candidate 606 is selected. In a defect candidate information window 602, a reference image 307-3, a detection image 307-2, a feature quantity 307-1 and the like of the selected defect candidate 606 are displayed. The window further displays a location of the selected defect candidate in the wafer or a location thereof in a cell. The user refers to the defect candidate information window 602 to determine whether the selected defect candidate is 'DOI' or 'Nuisance'. The user selects 'DOI' or 'Nuisance' in an instruction menu 604 in the defect candidate instruction window 603. In this case, the defect candidate information window 602 may also display an SEM image, optical microscope image and the like of the defect candidate 606 so that the user can determine the defect candidate to be 'DOI' or 'Nuisance' with reference to such images. The defect candidate instruction window 603 is equivalent to the instruction input unit 408.

The defect matrix creation unit 504 performs sampling in order to limit the defect candidates to be displayed in the defect matrix. The sampling is performed in a case where the defect matrix cannot display all the defect candidates such as when there are too many defect candidates. Examples of the sampling method include random sampling from the all defect candidates, sampling at given time intervals and the like. There is also known a method of sampling only the defect candidates around the classification boundary 406. The sampling can reduce the number of defect candidates which the user compares to give the instruction. This leads to the decrease in the burden on the user and the instruction time and to the improvement in the instruction correctness. Thus is provided user friendly DOI/Nuisance classification.

Figure 19:
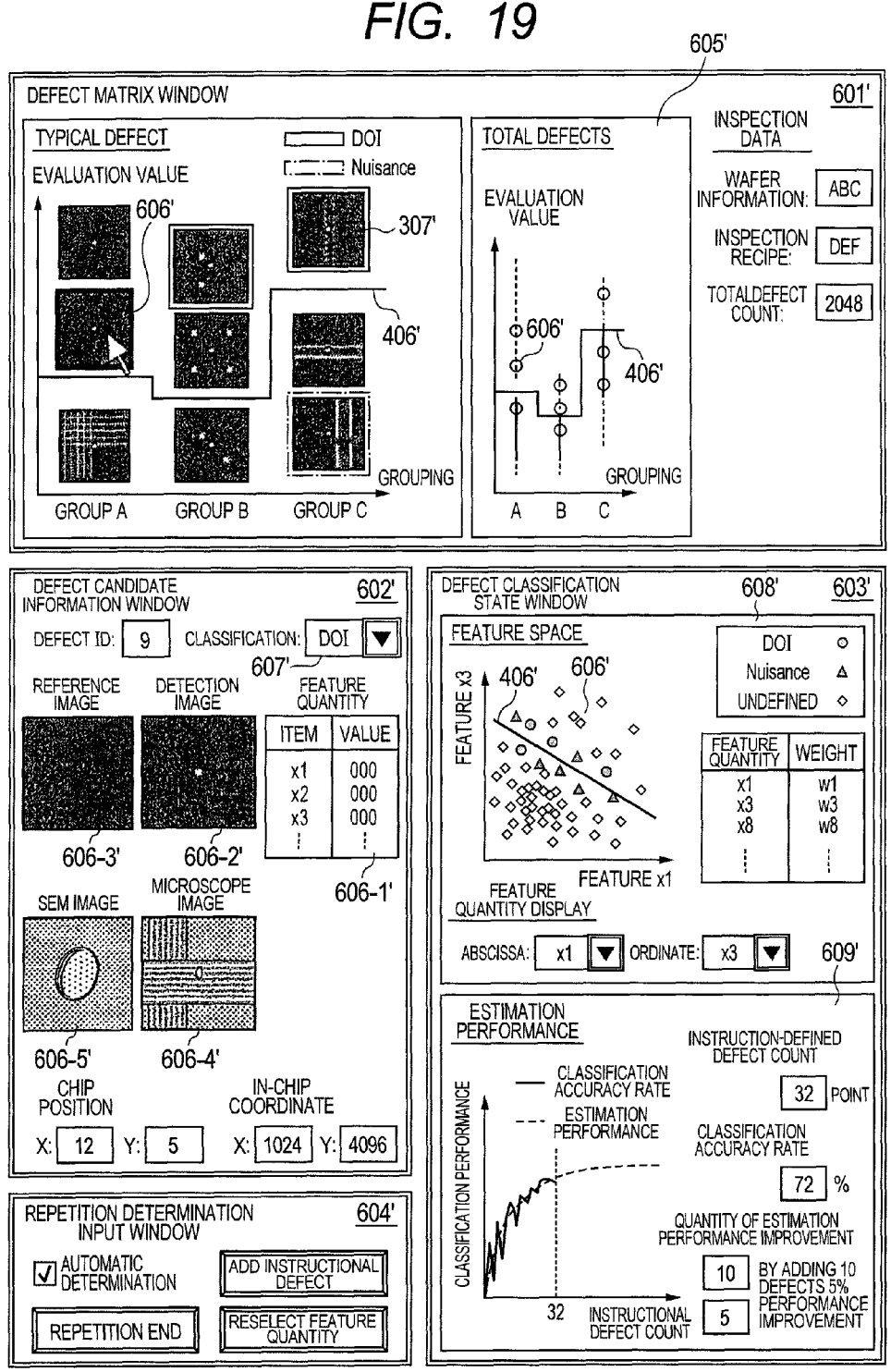
FIG. 19 is a diagram showing an exemplary modification of the defect candidate instructional GUI of the defect inspection device of the invention shown in FIG. 6.

FIG. 19 shows an exemplary modification of the defect candidate instructional GUI of the defect inspection device of the invention shown in FIG. 6.

The defect matrix creation unit 504, 506 shown in FIG. 5 or FIG. 17 displays the defect matrix in the defect matrix window (defect candidate window) 601 of the result display unit 407, 407'. The defect matrix shows arrays of defect candidate images each of which plots the group on the abscissa and the defect determination evaluation value on the ordinate. The defect matrix also shows the classification boundary 406' between 'DOI' and 'Nuisance'. The defect matrix window further displays a distribution window 605 showing the distribution of defect determination evaluation values of all the defect candidates on a per-group basis. The defect matrix window also shows, as inspection data, wafer information, inspection recipe, total defect count and the like. The user can select a defect candidate to which an instruction is given through the input device such as a mouse. FIG. 19 shows that a defect candidate 606' is selected. Displayed in a defect candidate information window 602' are a reference image 606-3', a detection image 606-2', a value feature 606-1' and the like of the selected defect candidate 606'. The window also shows a location of the selected defect candidate in the wafer or a location thereof in the cell. The user refers to the defect candidate instruction window 602' to determine whether the selected defect candidate is 'DOI' or 'Nuisance'. The user selects 'DOI' or 'Nuisance' through a defect candidate instruction window 607'. In this case, the defect candidate information window 602' may also display an SEM image 606-5' and optical microscope image 606-4' of the defect candidate 606' so that the user can determine the defect candidate to be 'DOI' or 'Nuisance' with reference to such images. When the defect classification is performed according to the above-described user's instruction, a defect classification state window 603' appears, showing the present state of classification. In the defect classification state window 603', a feature space window 608' shows a distribution of the defect candidates, a distribution of the defect candidates divided into those undefined by instruction and those defined by instruction, and the classification boundary 406' in the feature space including the selected feature quantities, as well as the selected feature quantities and weights thereof and the like. On the other hand, an estimation performance window 609' shows the instruction-defined defect count, the classification accuracy rate based on the instruction-defined defects and the quantity of estimation performance progress. The user checks the defect matrix window 601' and the defect classification state window 603' and decides on the need of adding the instructional defect and reselecting the feature quantity, inputting the decisions thus made to a repetition determination window 604'. The inspection device is also adapted for automatically determining on the repetition of the operation(s) and for permitting the user to select an automatic determination mode.

Figure 20:
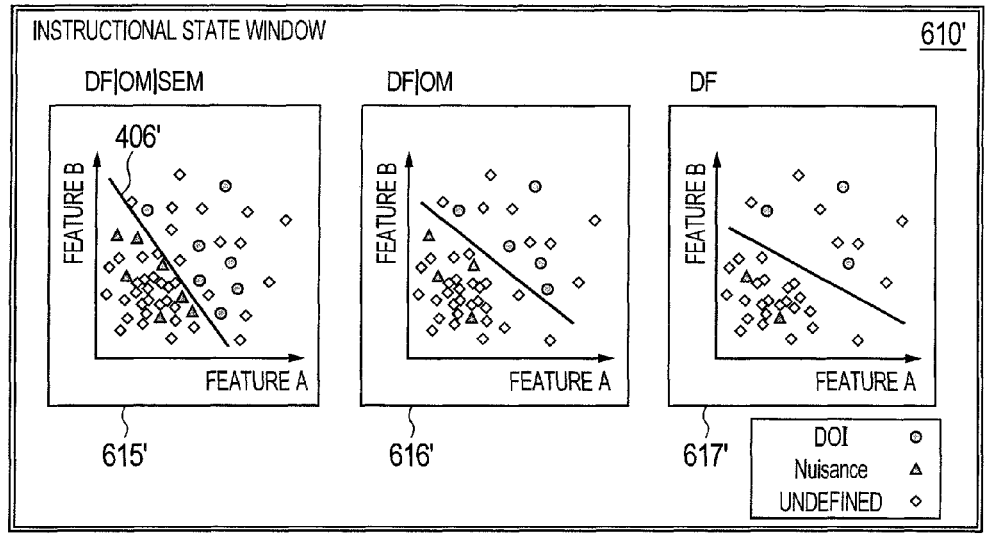
FIG. 20 is a diagram showing exemplary windows added to the defect candidate instructional GUI of the defect inspection device according to the invention.

FIG. 20 is a diagram showing exemplary windows added to the defect candidate instructional GUI of the defect inspection device according to the invention.

An addition window 609' is for display of additional information to those shown in the above-described defect candidate information window 602'. By visually checking the defect candidate images 606-2', 606-3', the user determines whether the defect candidate is 'DOI' or 'Nuisance' and gives the instruction via the defect candidate instruction window 607'. At this time, if the user cannot make determination based on only the defect candidate images 606-2', 606-3', the user can add an optical microscope image (OM image) 611' and a scanning electron microscope image (SEM image) 612' as information to assist in making determination. To add an image other than that of the defect candidate, the user may check a check box 613'.

The device, in turn, acquires the microscope image 611' and SE image 612' of the defect candidate selected through the check box and displays the acquired images in the defect candidate information window 609'. The user is permitted to determine how much the instruction made on the basis of the image other than that of the defect candidate is reflected in the subsequent classification and to input a corresponding numerical value to a classification influence rate input unit 614'. At this time, the user may input to the classification influence rate input unit a low value representing a fuzzy defect unclassifiable based on only the defect candidate information or may input a high value representing a defect of high reliability determined based on a plurality of information pieces.

Figure 7:
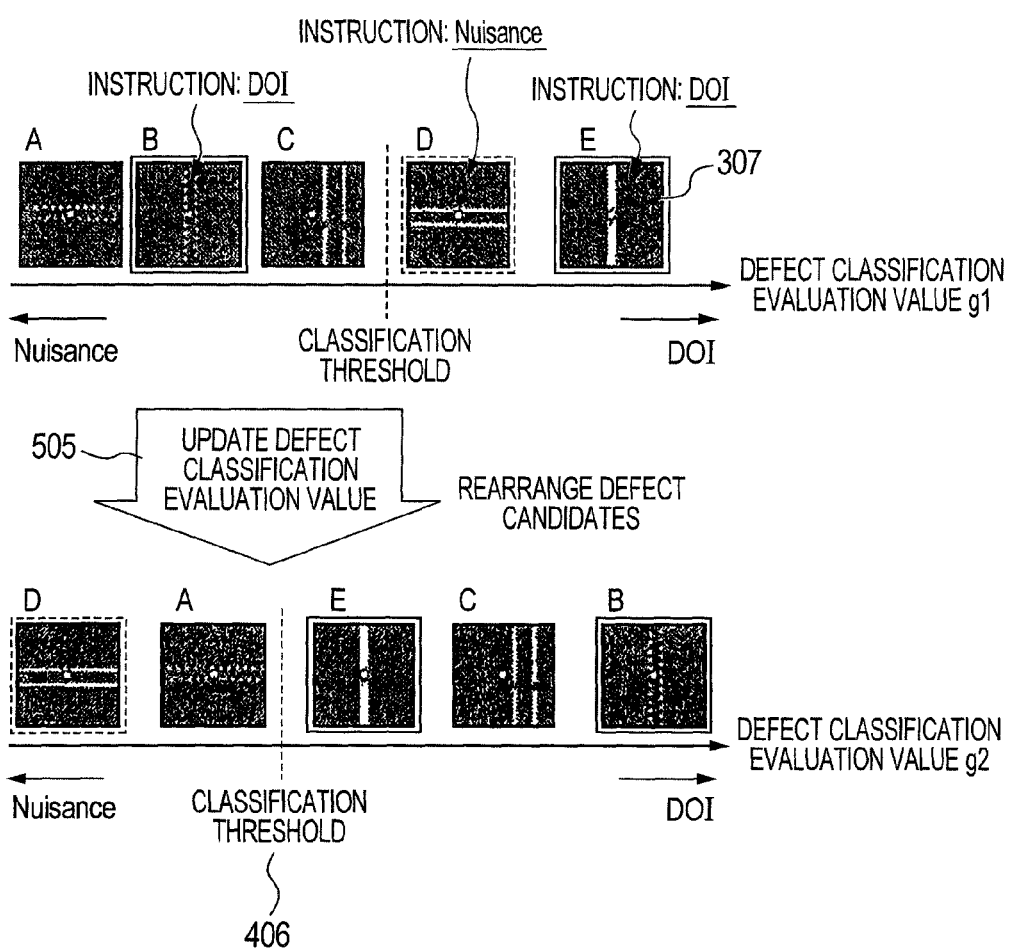
FIG. 7 is a diagram showing an exemplary DOI/Nuisance classification made on the basis of defect classification evaluation value updated by the defect inspection device according to the first embodiment of the invention.

When the classification is performed based on the defect candidates thus defined by the instruction, a distribution of feature quantities of the defect candidates and a classification boundary determined on the basis of the feature quantity distribution are displayed in an instructional state window 610'. A subwindow 615' in the instructional state window 610' shows defect candidates whose instructions are defined based on any one of DF, OM and SEM images and a classification boundary is determined on the basis of the defect candidates. A subwindow 616' shows defect candidates whose instructions are defined based on a DF image or OM image and a classification boundary is determined on the basis of the defect candidates. A subwindow 617' shows defect candidates whose instructions are defined based on only a DF image and a classification boundary is determined on the basis of the defect candidates. FIG. 7 is a diagram showing an exemplary DOI/Nuisance classification made on the basis of the defect classification evaluation value updated by the defect inspection device according to the first embodiment of the invention. The figure shows the contents of an updating processing for the defect classification evaluation value, which processing is performed by the defect classification evaluation value updating unit 505, 507 shown in FIG. 5 or FIG. 17. While the defect matrices shown in FIG. 6 and FIG. 18 plot the defect determination evaluation value on the ordinate, the figure shows the defect determination evaluation values on the horizontal axis (abscissa) for illustrative purpose. Provided that defect candidates A, B, C, D, E are arranged based on the defect classification evaluation values $g1=i1(x1, x2, ...)$, it is assumed in this case that the user inputs to the instruction input unit 408, 408' an instruction that the defect candidates B and E are 'DOI' and the defect candidate D is 'Nuisance'. The defect classification threshold determination unit 506 of FIG. 5 or the defect classification boundary determination unit 508 of FIG. 17 sets a classification threshold for DOI/Nuisance classification of the defect candidate to one of the defect classification evaluation values 'g'. Whatever value is the threshold set to, correct classification cannot be achieved.

Hence, the defect classification evaluation value updating unit 505, 507 of FIG. 5 or FIG. 17 changes the feature quantity integration function i1 to i2, updating the defect classification evaluation value to $g2=i2(x1, x2, ...)$. The following methods can be used for updating the evaluation value. In a case where the feature quantity integration function it is expressed as weighted linear sum $i1(x1, x2, x3)=w1 \cdot x1+w2 \cdot x2+w3 \cdot x3$, for example, the weighting parameters for the weights w1, w2, w3 can be changed. Otherwise, the function 'i' itself can be changed to square sum $i2=(x1,x2,x3)=w1 \cdot x1^2+w2 \cdot x2^2+w3 \cdot x3^2$ (^ denotes the power).

The evaluation values are updated by the defect classification evaluation value updating unit 505 so that the defect candidates A, B, D, D, E are rearranged as D, A, E, C, B. Thus is obtained the threshold value that classifies the defect candidates B, E as 'DOI' and the defect candidate D as 'Nuisance'. The defect classification evaluation value updating unit 505 can provide updated defect classification evaluation values varying from group to group and can also provide the same update on all the groups. Namely, the defect classification evaluation value may vary from group to group or the same defect classification evaluation value may be shared by all the groups.

The defect classification threshold determination unit 506 determines a threshold value for the DOI/Nuisance classification of the defect candidates of each group which are arranged in the order of evaluation value. The threshold value is so defined as to distinguish between 'DOI' and 'Nuisance' as instructed by the user and can be applied to common classification methods. Examples of the applicable classification method include classification according to decision tree, classification using support vector machine, classification based on nearest neighbor rule and the like.

The threshold value may vary from group to group or the same threshold value may be shared by all the groups. Furthermore, the defect classification threshold determination unit 506 can automatically determine the threshold value. The user can repeat the sequence of steps of updating the defect classification evaluation value (505) in multiple cycles by operating the matrix result display unit 407 and the instruction input unit 408, thereby accomplishing the flexible DOI/Nuisance classification based on the judgment criteria varying from user to user.

Figure 21:
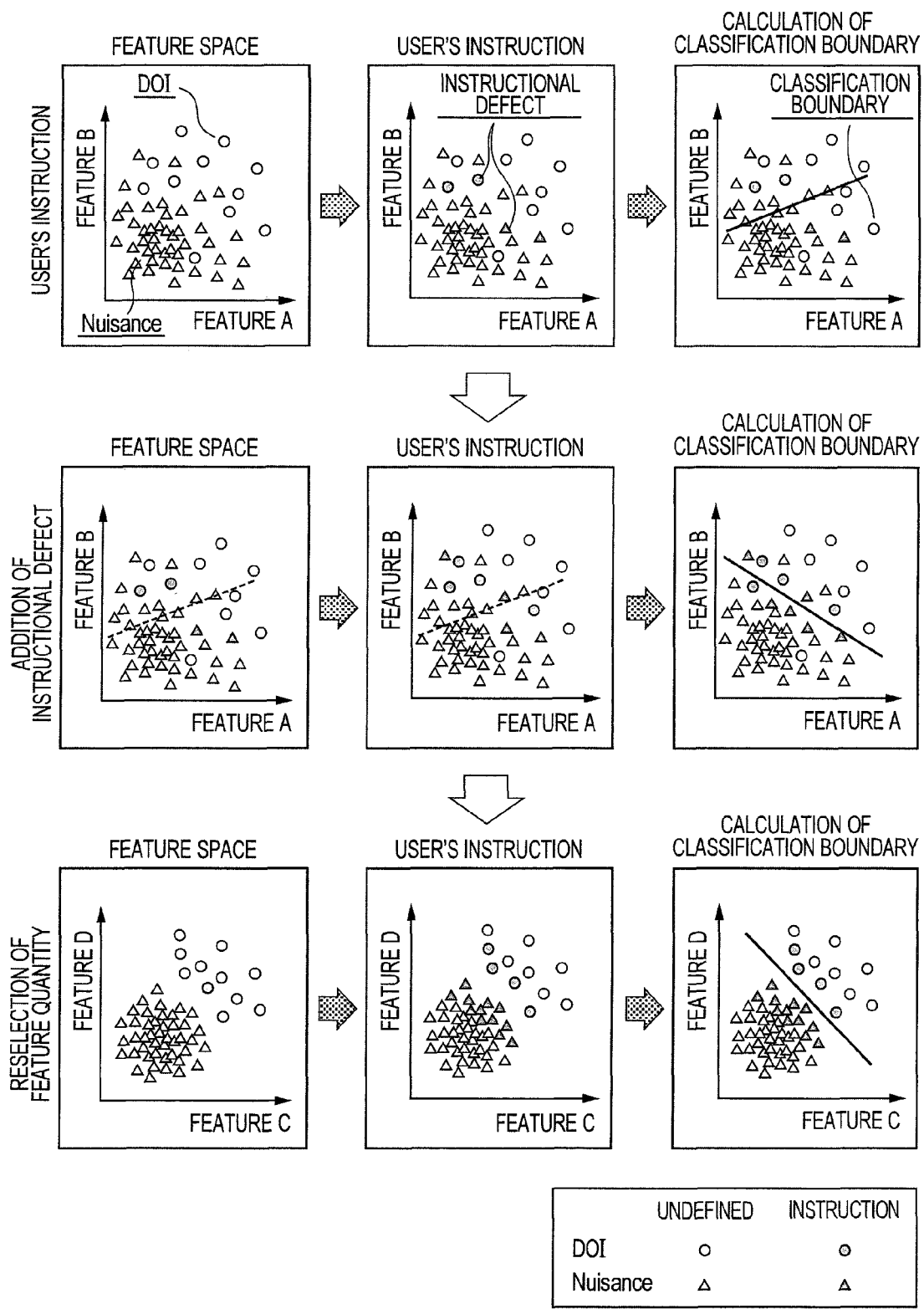
FIG. 21 is a group of diagrams showing the change in classification boundary as a result of the addition of instructional image and the reselection of feature quantity in the defect inspection device according to the first embodiment of the invention.

FIG. 21 is a group of diagrams showing the change in classification boundary as a result of the addition of instructional image and the reselection of feature quantity in the defect inspection device according to the first embodiment of the invention. Particularly, the figure shows the change in the classification boundary, which change results from the addition of defect defined by the user's instruction, and the change in DOI/Nuisance distribution in the feature space, which change results form the reselection of the feature quantity. An upper row of diagrams in FIG. 21 show how the user's instruction is given to some of the undefined defect candidates so that the classification boundary is determined on the basis of the instruction-defined defects. A middle row of diagrams in FIG. 21 shows how the classification boundary shown in the upper row of diagrams is updated by adding the defects defined by the user's instruction. However, the classification performance is not improved by further adding the instructional defects to the state shown in the middle row of diagrams. Hence, the feature quantity is reselected to change the defect distribution in the feature space, which change entails change in the classification boundary. This change process is shown in a lower row of diagrams in FIG. 21. The classification performance can be improved by adding the instructional defect and reselecting the feature quantity.

Figure 8:
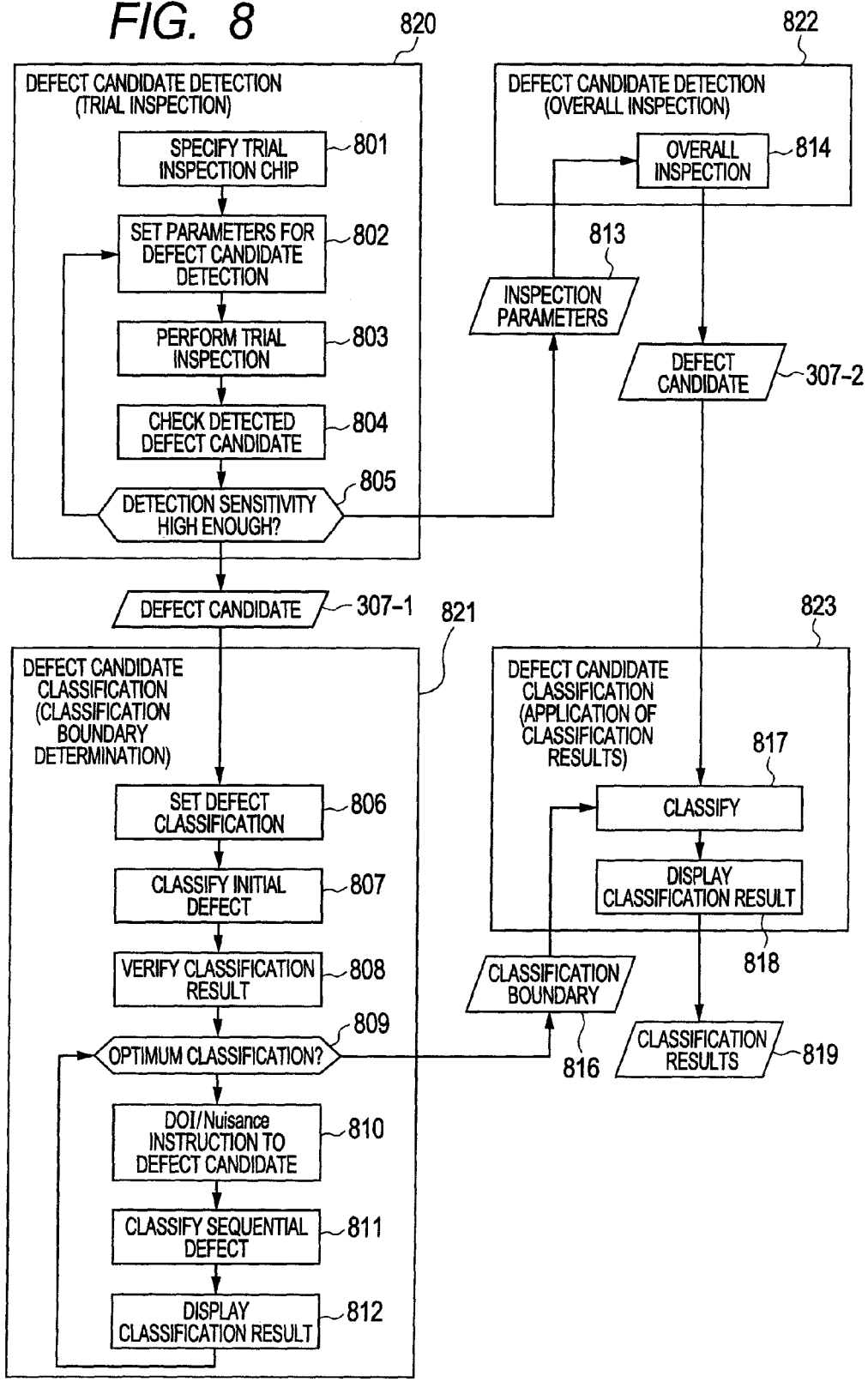
FIG. 8 is a flow diagram showing the steps of an exemplary defect inspection operation performed by the defect inspection device according to the first embodiment of the invention.

FIG. 8 is a flow diagram showing the steps of an exemplary defect inspection operation performed by the defect inspection device according to the first embodiment of the invention. The figure shows the flow of steps of the operations by the defect candidate detection unit 100 and the post-inspection processing unit 108. After permitting the user to specify a trial inspection chip (801) and to set parameters (802), the defect candidate detection unit 100 performs a trial inspection (803). The trial inspection (820) means an inspection method wherein an inspection is performed on a partial area of the wafer and inspection parameters are so set as to provide a proper ratio between real defects and false defects detected therefrom.

The post-inspection processing unit 108 performs defect classification (807) on the defect candidates (value features) (307-1) detected by the trial inspection. After checking the classification results (808), the post-inspection processing unit displays to the user the classification results in the form of the defect matrix 601. Based on the displayed results, the user gives the DOI/Nuisance instruction to the individual defect candidates (810). The user determines whether an optimum classification is accomplished or not (809). The results display (812) and the user input instruction (810) are repeated till a defect classification desired by the user is obtained (811).

Subsequently, the inspection (814) is performed on the overall surface of the wafer using the inspection parameters 813 set by the trial inspection. Defect candidates detected by the overall inspection are classified into 'DOI' or 'Nuisance' (817) using the classification boundary 816 determined by the defect candidate classification (821). The classification results are displayed to the user (818).

While the above embodiment provides the user input instruction for updating the defect classification evaluation value, the user input instruction may also be provided for grouping of the defect candidates.

Figure 9:
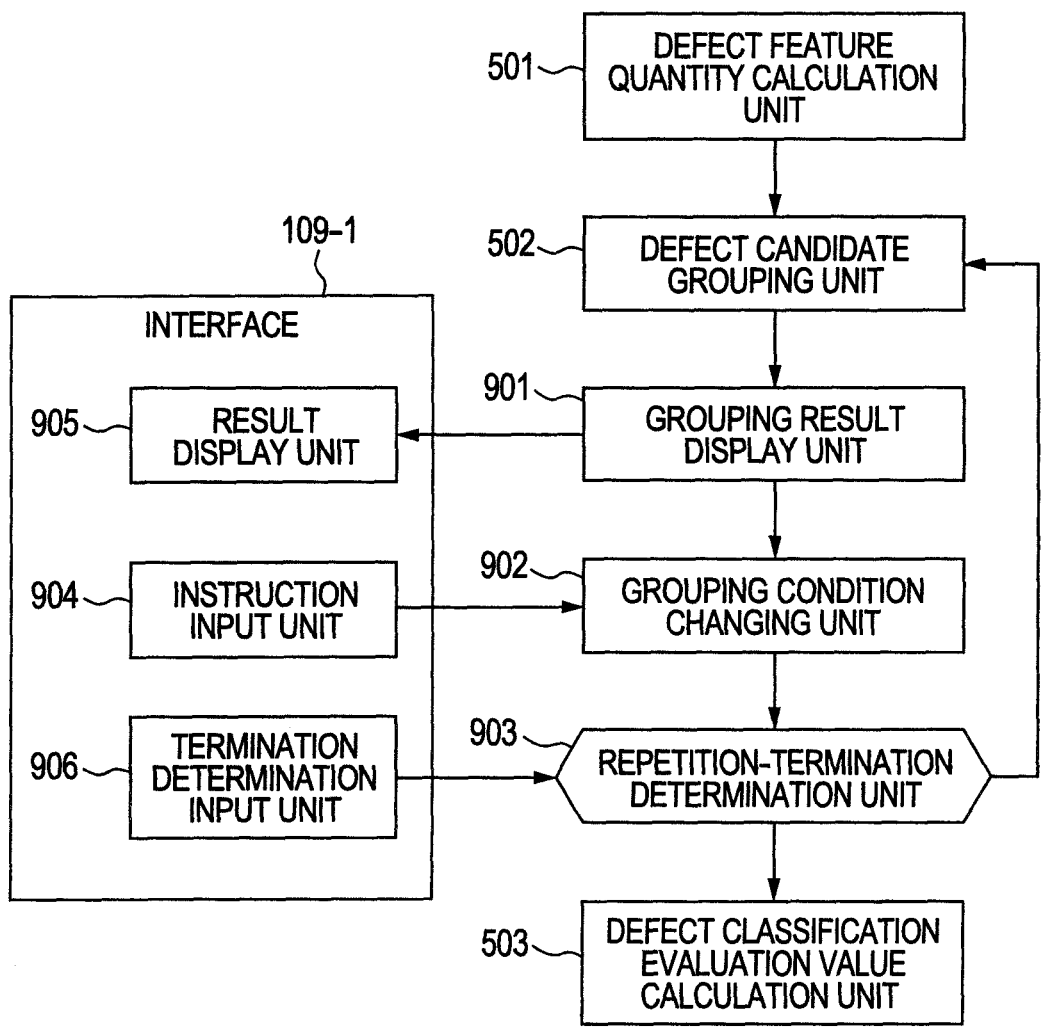
FIG. 9 is a diagram showing an exemplary grouping of defect candidates on the basis of the user's instruction inputted to the defect inspection device according to the first embodiment of the invention.

FIG. 9 shows an exemplary grouping of the defect candidates on the basis of the user's instruction inputted to the defect inspection device according to the first embodiment of the invention. A grouping result display unit 901, a grouping condition changing unit 902 and a repetition-termination determination unit 903 are added to the defect candidate grouping unit 502.

The defect candidate is inputted to the defect classification calculation unit 404 while the defect feature quantity calculation unit 501 outputs a feature quantity of the defect candidate. The defect feature quantity calculation unit 501 calculates the feature quantity while the defect candidate grouping unit 502 groups the defect candidate into a similar-defect group on the basis of the feature quantity thus calculated. The grouping criteria include (1) similarity of the reference images (background image), (2) proximity between the defect candidates, (3) defect configuration similarity of the defect candidates and the like.

The feature quantity used for grouping the defect candidates includes: (1) luminance, (2) contrast, (3) brightness difference, (4) luminance variance of neighboring pixels, (5) correlation coefficient, (6) increase or decrease in luminance from that of neighboring pixel, (7) secondary differentiation value and the like. The grouping result is displayed to the user, who instructs a correct group if the grouping result is not correct.

Figure 22:
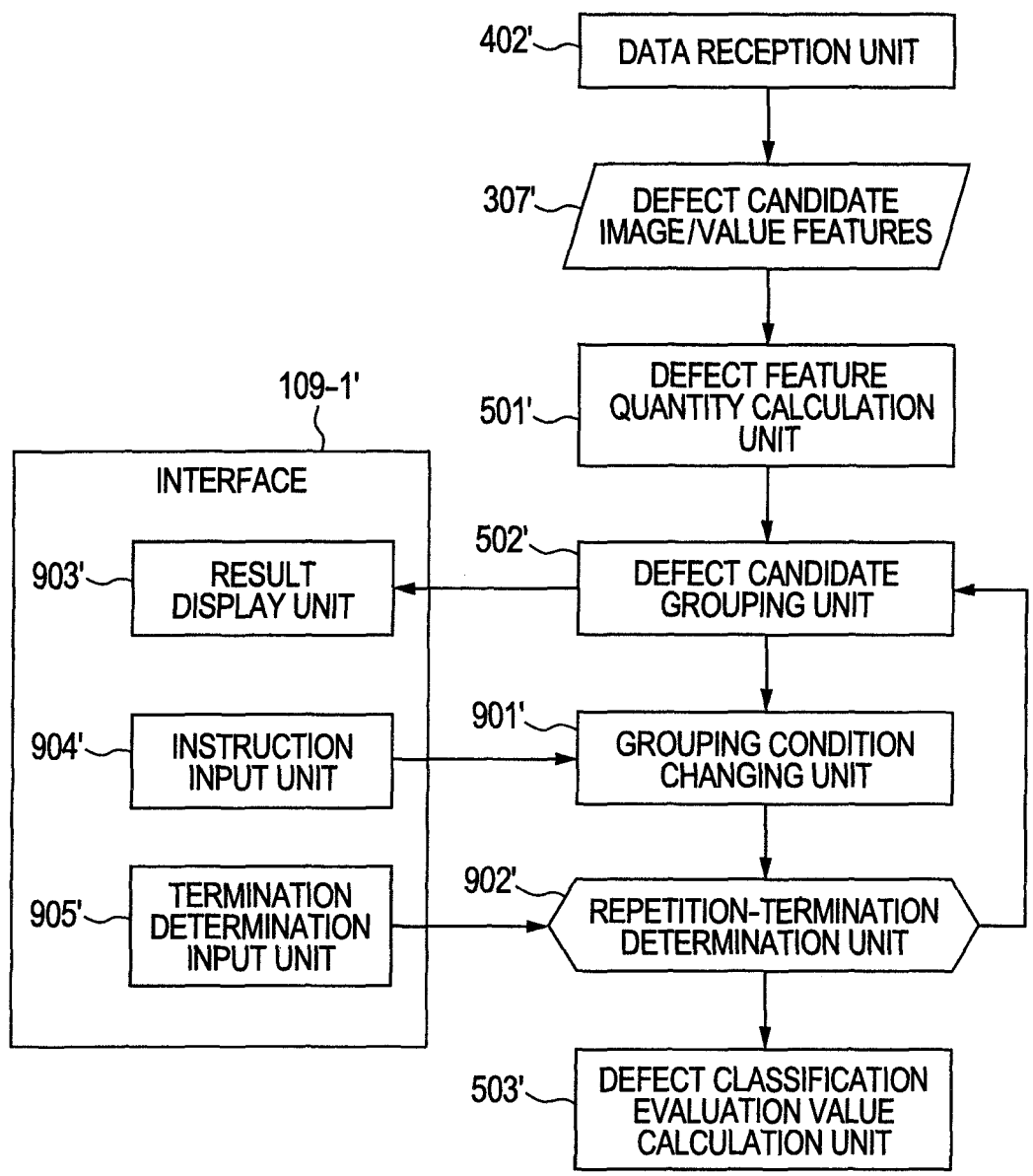
FIG. 22 is a diagram showing an exemplary modification of the defect candidate grouping on the basis of the user's instruction inputted to the defect inspection device according to the first embodiment of the invention shown in FIG. 9.

FIG. 22 shows an exemplary modification of the defect candidate grouping on the basis of the user's instruction inputted to the defect inspection device according to the first embodiment of the invention shown in FIG. 9.

A grouping condition changing unit 901' and a repetition-termination determination unit 902' are added to a defect candidate grouping unit 502'.

Similarly to the first embodiment, the data reception unit 402' inputs the defect candidate 307' to a defect feature quantity calculation unit 501'. The defect feature quantity calculation unit 501' calculates a feature quantity of the defect candidate 307'. On the basis of the calculated feature quantity, the defect candidate grouping unit 502' groups the defect candidate into a similar-defect group. The grouping result is displayed to the user via a result display unit 903'. If the grouping result is not correct, the user inputs a correct group to the grouping condition changing unit 901' by means of an instruction input unit 904'.

Figure 10:
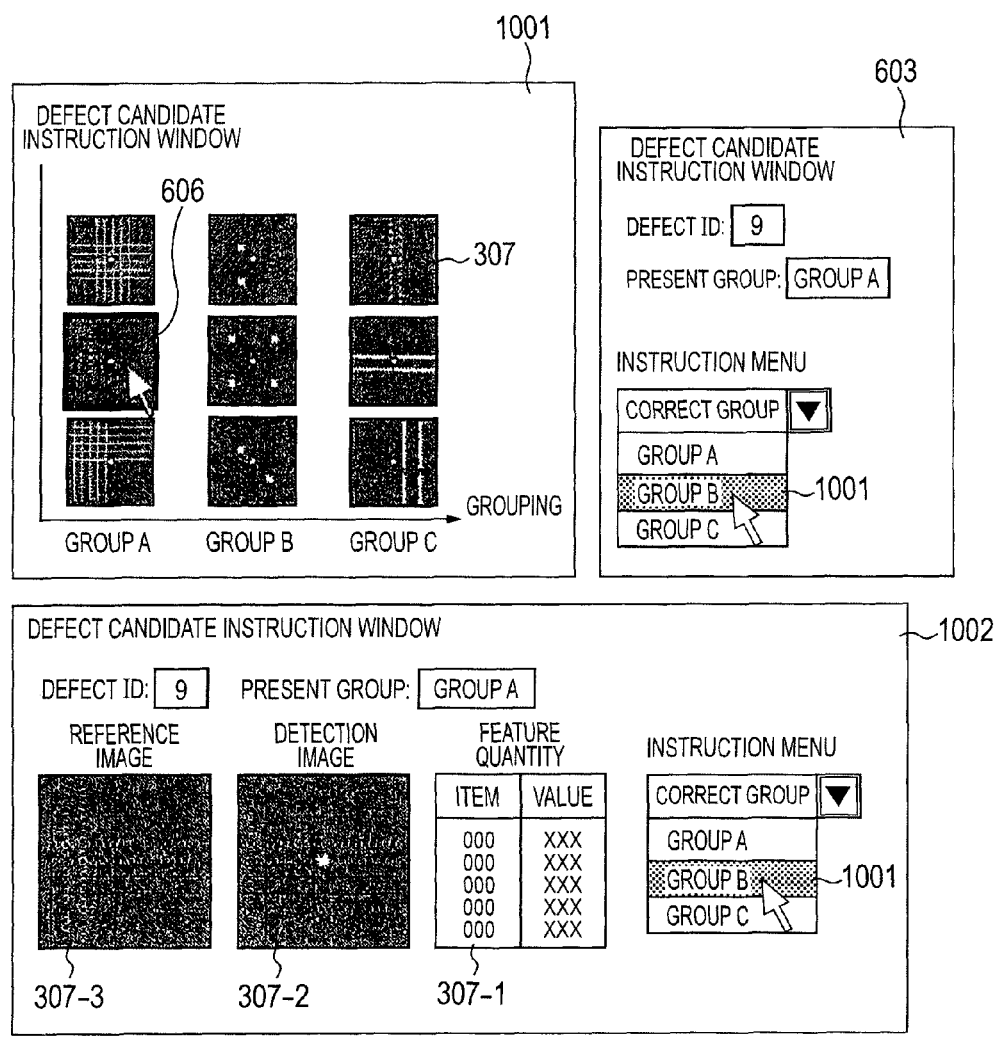
FIG. 10 is a diagram showing an exemplary defect candidate instructional GUI for defect candidate grouping performed by the defect inspection device according to the first embodiment of the invention.

FIG. 10 is a diagram showing an exemplary defect candidate instructional GUI for defect candidate grouping performed in the defect inspection device according to the first embodiment of the invention. An incorrectly grouped defect candidate is selected from a group determined by the defect candidate grouping unit 502. The user selects a correct group by referring the reference image 307-3 shown in a defect candidate instruction window 1002. This selection operation is performed at the instruction input unit 904. The defect candidate grouping unit 502 uses a commonly used pattern identification method as a grouping method. Examples of the applicable pattern identification method include classification according to decision tree, classification using support vector machine, classification based on nearest neighbor rule and the like. These methods require learning of grouping conditions in advance. On the basis of the instruction of the correct group, the grouping condition changing unit 902 defines a new grouping condition for a pattern identification process. Subsequently, the defect candidate is grouped again on the basis of the new grouping condition and the result is displayed to the user. These operations are repeated till the user is satisfied with the grouping result. At this time, the user decides to terminate the repetition operations and inputs 'repetition end' to a termination determination input unit 906 so that the repetition-termination determination unit 903 terminates the repeated operations.

A more accurate grouping is accomplished by giving the instruction to the grouping of the defect candidates. This enables a more accurate DOI/Nuisance classification in determining the defect classification threshold or defect classification boundary for each group.

In the above embodiment, the defect matrix creation unit 504 creates the defect matrix on the basis of the results of the grouping by the defect candidate grouping unit 502 and the defect classification evaluation values calculated by the defect classification evaluation value calculation unit 503, and displays the defect matrix to the user. The user in turn gives the instruction on the defect matrix via the user interface 109-1 whereby the classification of the defect candidates is accomplished.

The above embodiment accomplishes the defect classification by way of the defect candidate grouping and the user-input instruction. Here is illustrated an example where the user-input instruction is not provided and where the defect candidates are classified into 'DOI' or 'Nuisance' on the basis of previous data such as a previously defined DOI feature quantity and a feature quantity calculated from the defect candidate.

Figure 11:
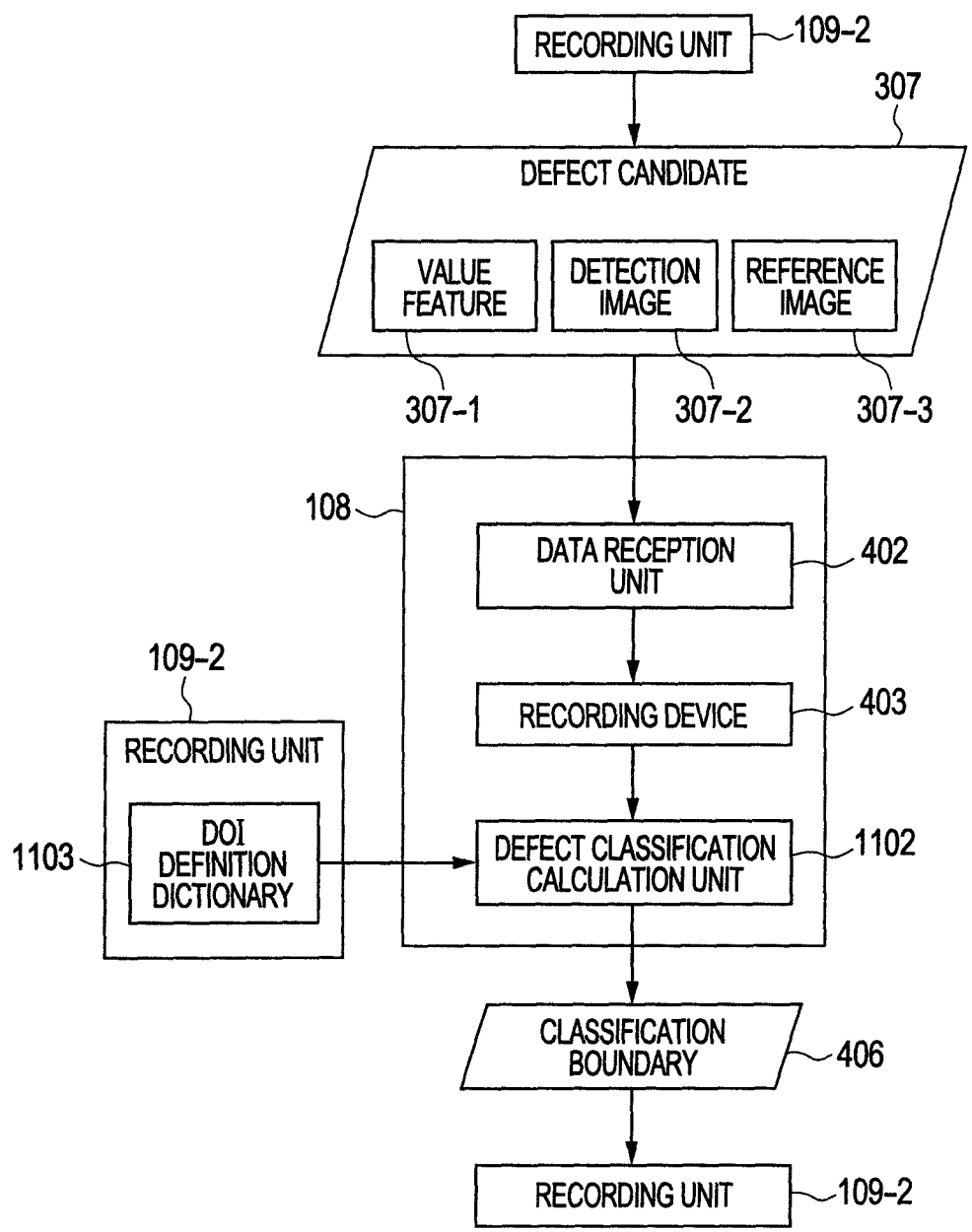
FIG. 11 is a diagram showing an exemplary arrangement of the post-inspection processing unit employing a DOI definition dictionary and disposed in the defect inspection device according to the first embodiment of the invention.

FIG. 11 is a diagram showing an exemplary arrangement of the post-inspection processing unit employing a DOI definition dictionary and disposed in the defect inspection device according to the first embodiment of the invention. An embodiment of the post-inspection processing unit that does not provide the instruction is described as below. Similarly to the above first embodiment, the defect candidate 307 (defect value feature 404-1, clipped image from the detection image 404-2, and clipped image from the reference image 404-3) is inputted to the data reception unit 402 and stored in the recording device 403. The feature of the defect candidate stored in the recording device 403 is compared with a feature of the DOI contained in a DOI definition dictionary 1103 stored in the recording unit (recording device) 109-2 of the main control unit so as to classify the defect candidate into 'DOI' or 'Nuisance'. The DOI definition dictionary 1103 stores defect candidates defined as 'DOI' or 'Nuisance' and feature quantities extracted from the defect candidates, which are previously inputted by the user. The DOI definition dictionary 1103 may also store previously determined DOI/Nuisance classification boundaries. The DOI definition dictionary 1103 may also containing design information 307-4 on the sample 101 which corresponds to the defect candidate 307' in FIG. 16.

Figure 12:
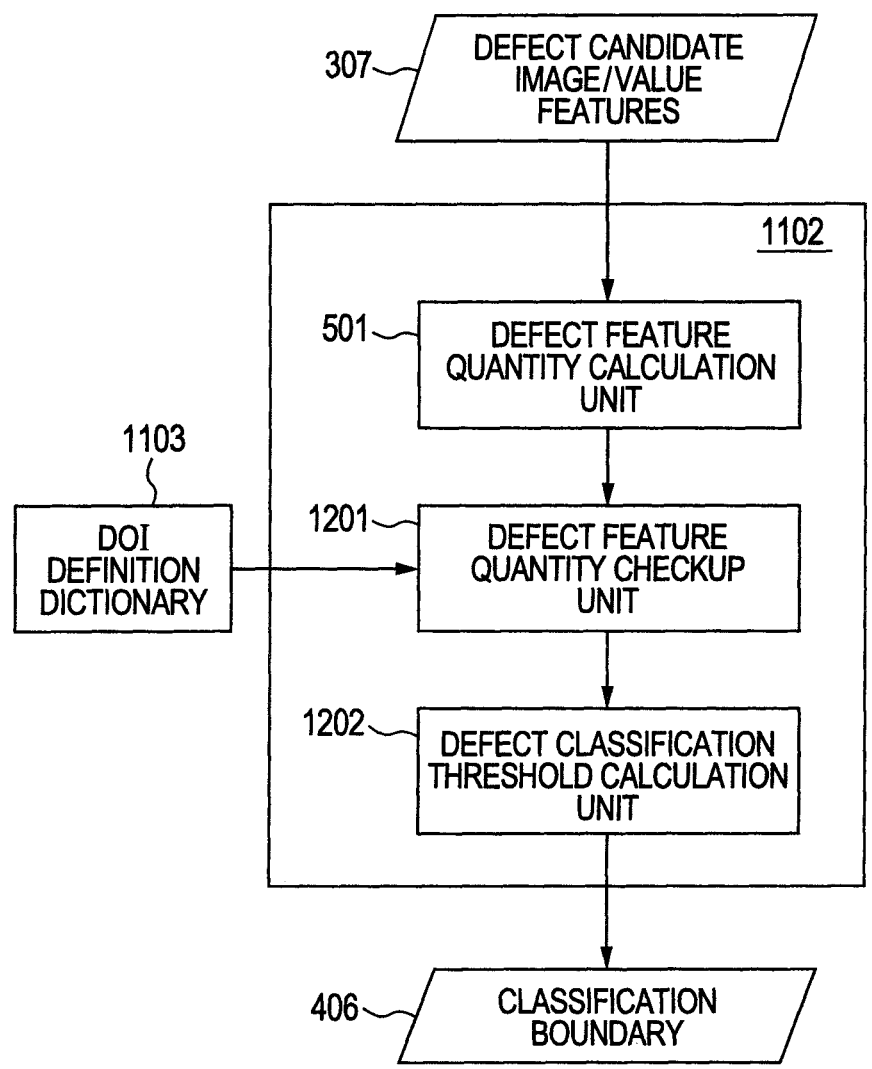
FIG. 12 is a diagram showing an exemplary arrangement of the defect classification calculation unit employing the DOI definition dictionary and disposed in the defect inspection device according to the first embodiment of the invention.

FIG. 12 is a diagram showing an exemplary arrangement of the defect classification calculation unit employing the DOI definition dictionary and disposed in the defect inspection device according to the first embodiment of the invention. The defect feature quantity calculation unit 501 calculates a feature quantity from a defect candidate 307 inputted thereto. The feature quantity used for the defect classification includes: (1) luminance, (2) contrast, (3) brightness difference, (4) luminance variance of neighboring pixels, (5) correlation coefficient, (6) increase or decrease in luminance from that of neighboring pixel, (7) secondary differentiation value and the like. A defect feature quantity checkup unit 1201 compares the DOI feature quantity stored in the DOI definition dictionary 1103 with the feature quantity of the defect candidate 307. The nearest neighbor rule, the support vector machine or the like generally used in the art may be used for the comparison of the feature quantities. A defect classification threshold calculation unit 1202 (defect classification boundary calculation unit) determines whether the defect candidate 307 is 'DOI' or 'Nuisance' and calculates the classification boundary 406.

In this embodiment, the defect judgment is made using the DOI definition dictionary 1103 instead of providing the user-input instruction. In the defect inspection during the mass-production of semiconductor wafers, therefore, inspection sensitivity variations due to the judgment criteria varying from user to user can be reduced, further, the instruction time and the calculation time for defect classification can be reduced. Thus, the defect inspection can be speeded up.

Next, another example of the defect inspection device of the invention which includes an image processing system having the above-described structure is described by way of example where the defect candidates are classified using stored information on the past classification. A defect classification database includes information corresponding to : (1) classification boundary, (2) feature quantities of individual defect candidates, (3) selected feature quantities, (4) results of instruction to selected defect candidates, (5) grouping criteria and the like, which are the defect classification results outputted in the past. These information pieces are used for the classification.

Figure 23:
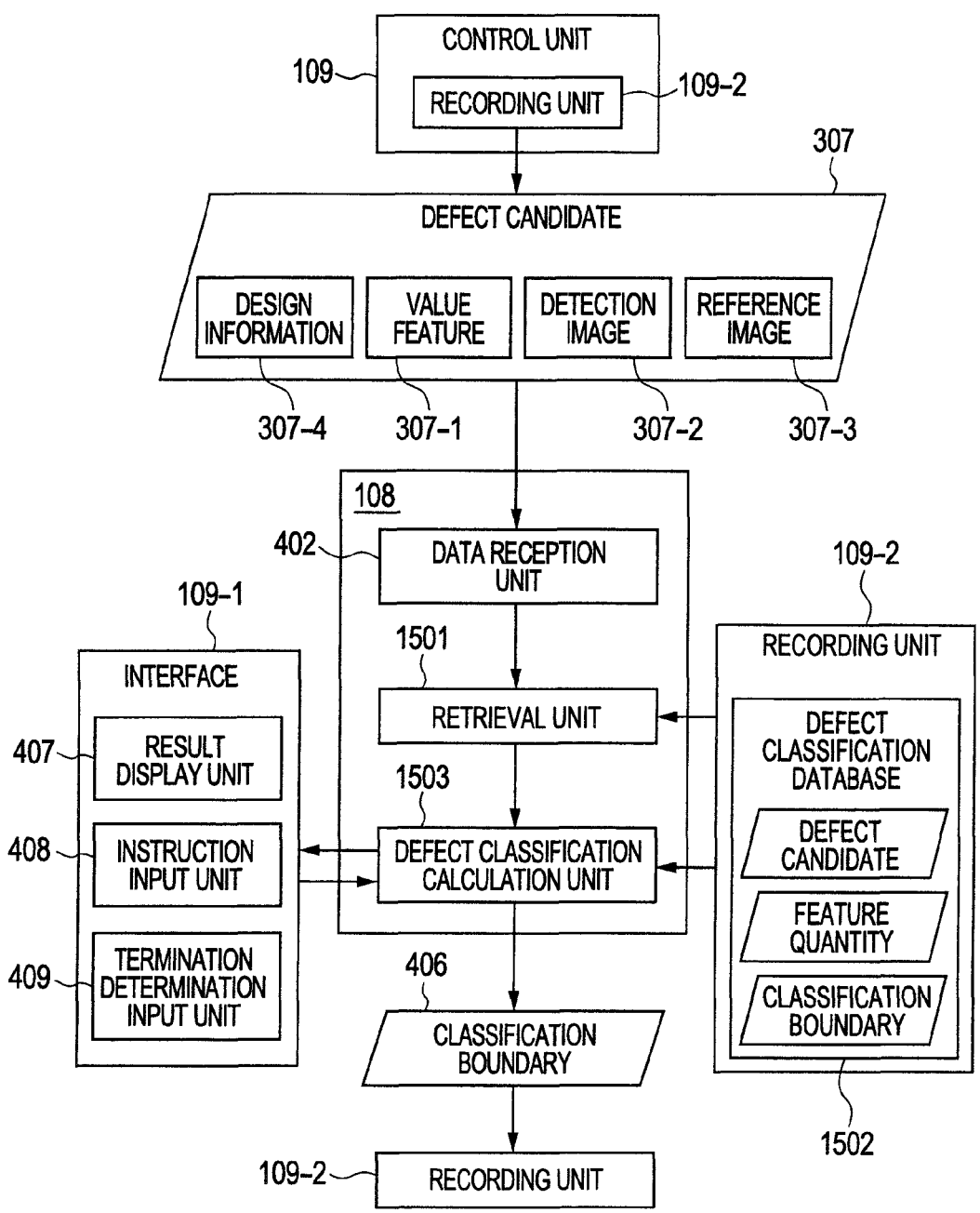
FIG. 23 is a diagram showing an arrangement of a post-inspection processing system which uses a defect classification database.

FIG. 23 shows an arrangement of a post-inspection processing system which uses the defect classification database. Similarly to the above first embodiment, the defect candidate 307 (defect value feature 307-1, clipped image from the detection image 307-2, and clipped image from the reference image 307-3 and design information 307-4) is inputted to the data reception unit 402. A retrieval unit 1501 receives from the data reception unit 402 the defect candidate 307 as a classification object and retrieves a defect candidate resemblant to the above defect candidate 307 from a group of classified defect candidates stored in a defect classification database 1502. The retrieval of the above-described defect candidate may be carried out based on (1) information on the type and fabrication process of the sample 101, (2) similarity of the detection images, (3) similarity of feature quantity distributions and the like. Otherwise, the user may also specify a defect candidate resemble to the defect candidate 307 among the group of classified defect candidates stored in a defect classification database 1502. A defect classification calculation unit 1503 performs the defect classification on the basis of: (1) the classification boundary of the resemblant defect candidate, (2) the feature quantity of each defect candidates, (3) the selected feature quantity, (4) the result of instruction to the selected defect candidate, (5) the grouping criteria and the like as well as the user input via the user interface 109-1. The obtained classification boundary 406 is outputted to the recording unit 109-2.

Figure 24:
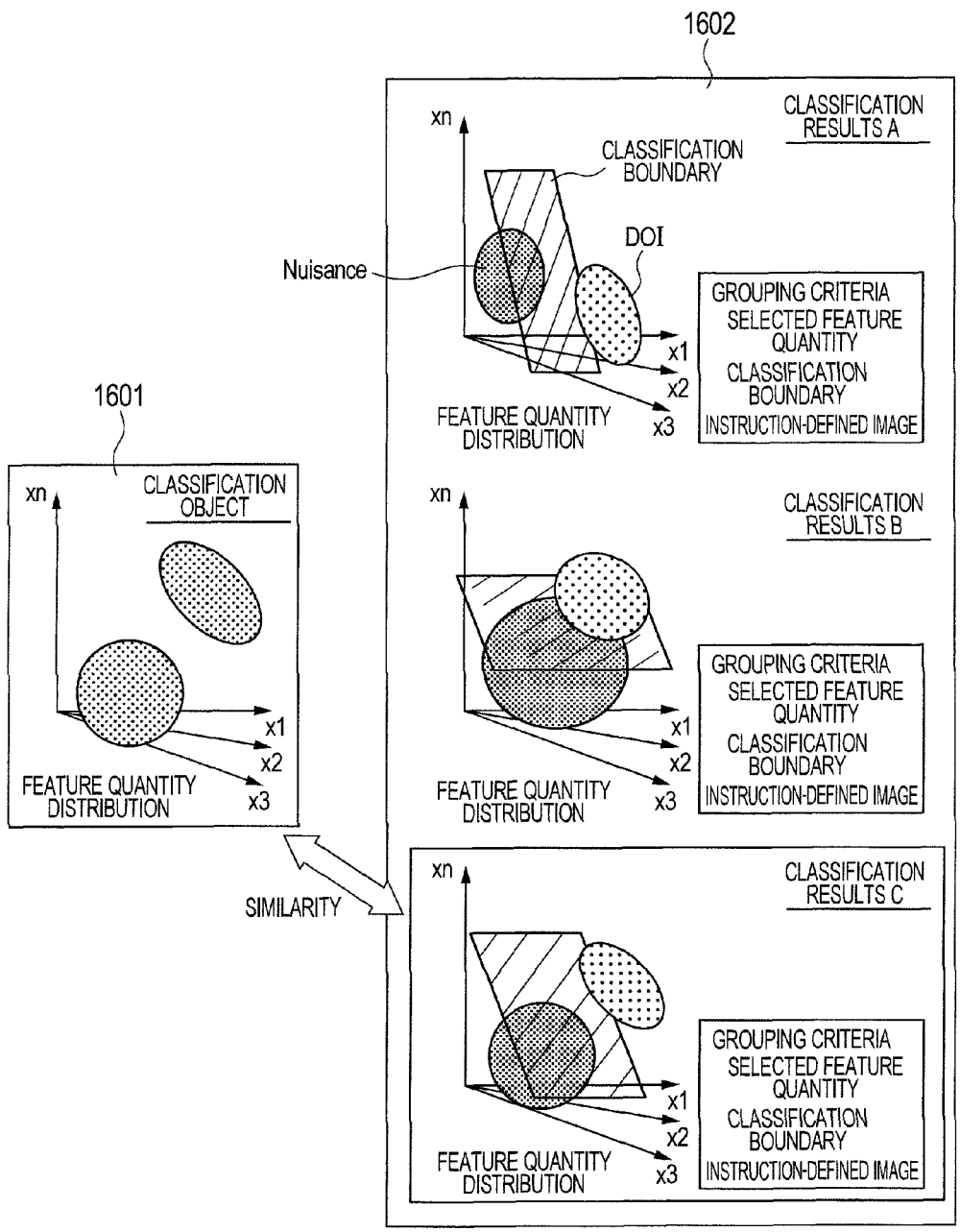
FIG. 24 is a diagram showing an exemplary retrieval result on the basis of comparison of feature quantity distributions.

FIG. 24 is a diagram showing an exemplary retrieval result on the basis of comparison of feature quantity distributions. A defect candidate having a feature quantity distribution similar to that of a classification object 1601 is retrieved from a group 1602 of defect candidates classified in the past. The retrieval is carried out on the basis of the evaluation of the degree of similarity between the feature quantity distribution of the defect candidate 1601 as the classification object and each of the feature quantity distributions of classification result A, classification result B and classification result C. The degree of similarity is evaluated on the basis of (1) the sum of distances between the nearest defect candidates as determined when defect candidates to be compared are overlapped with each other, (2) the comparison between local defect densities in the feature space, and the like. In the case shown in FIG. 17, the classification result C is selected as the retrieved defect candidate on the basis of the evaluation of the similarity degree. The grouping criteria, selected feature quantity, classification boundary or the like of the retrieved defect candidate is used for the DOI/Nuisance classification by a defect classification calculation unit to be described hereinafter.

Figure 25:
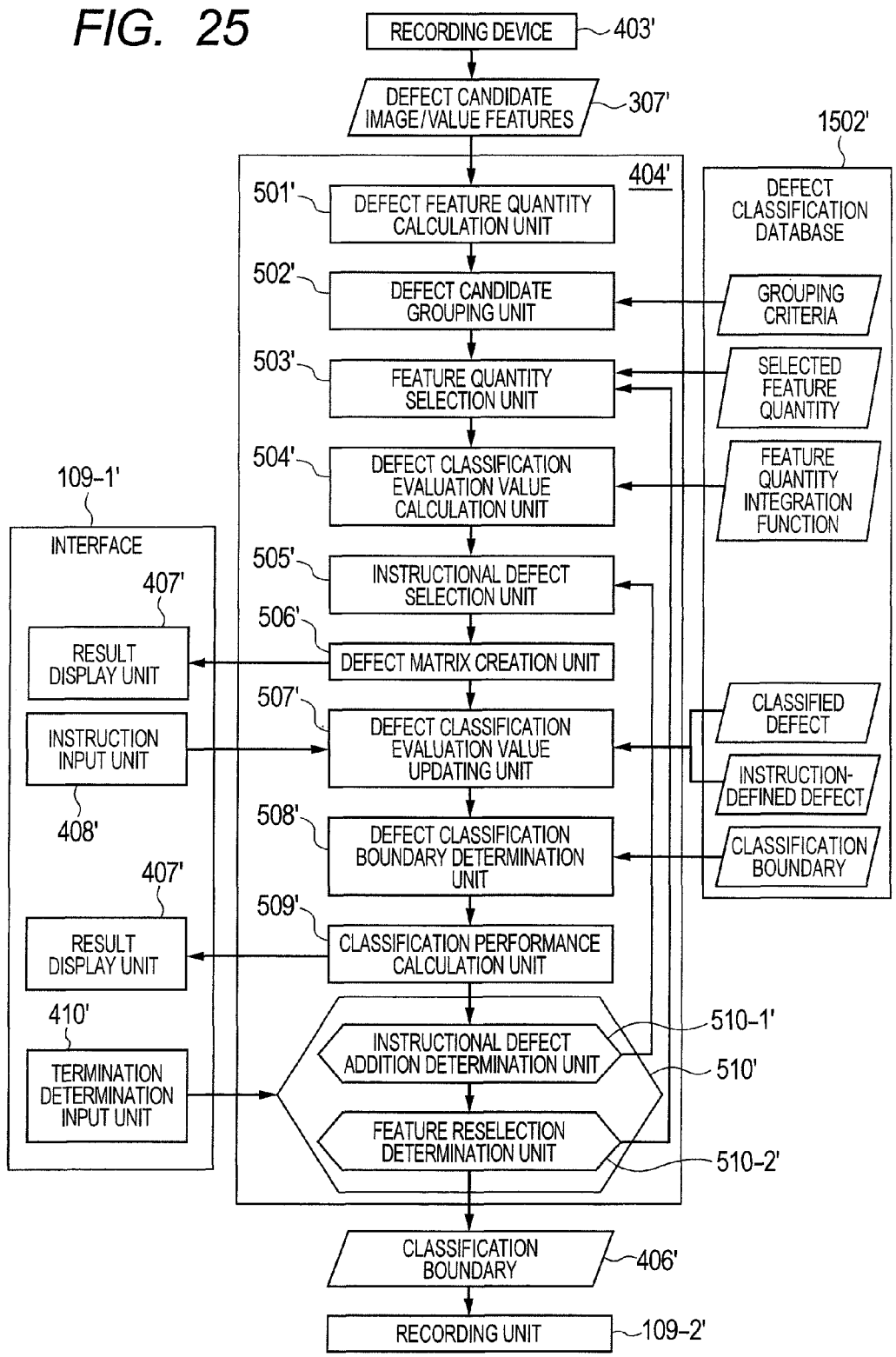
FIG. 25 is a diagram showing an exemplary arrangement of the defect classification calculation unit using the defect classification database and disposed in the defect inspection device according to the first embodiment of the invention.

FIG. 25 is a diagram showing an exemplary arrangement of the defect classification calculation unit using the defect classification database and disposed in the defect inspection device according to the first embodiment of the invention. In an operation flow of the DOI/Nuisance classification, the description of the same operations as those of the above-described embodiment is omitted. The defect classification database can provide input of the grouping criteria to the defect candidate grouping unit 502', input of combination of feature quantities effective for the classification to a feature quantity selection unit 503', input of the feature quantity integration function for the calculation of the defect classification evaluation value to a defect classification evaluation value calculation unit 504', and input of the classified defect and instruction-defined defect, rather than the user-input instruction, to a defect classification evaluation value updating unit 507', and input of the classification boundary to a classification boundary determination unit 508'.

FIG. 26 is a group of diagrams for explaining a method wherein classified defects are used for instructional purpose. A defect candidate 1703 having the nearest classification result to a defect candidate 1702 in the feature space is referred to (1701) so as to assign 'DOI' or 'Nuisance', instead of the user-input instruction, to the defect candidate 1702 which is a classification object and is undefined by instruction. Alternatively, a defect candidate 1705 effective for the classification is extracted from the defect candidates of the classification result and is inserted in the feature space of the classification object. The classification boundary 406 can be determined on the basis of the inserted defect candidate (1704). A classification boundary newly determined using the defect classification database is an output relatively resemblant to a classification boundary stored in the defect classification database and hence, the classification result variations in one device or between different devices can be reduced. Furthermore, the burden on the user can be reduced because the use of the defect classification database leads to the reduction of the number of instructional defects or permits the classification to be accomplished without the aid of the instruction. In addition, the processing time can also be reduced because the classification boundary can be determined without repeating the instruction input and classification operations.

Second Embodiment

Next, another embodiment of the defect inspection device including the image processing system having the above-described system structure is described by way of example where the inspection device includes a plurality of illumination optical systems and detection optical systems for image detection.

Figure 13:
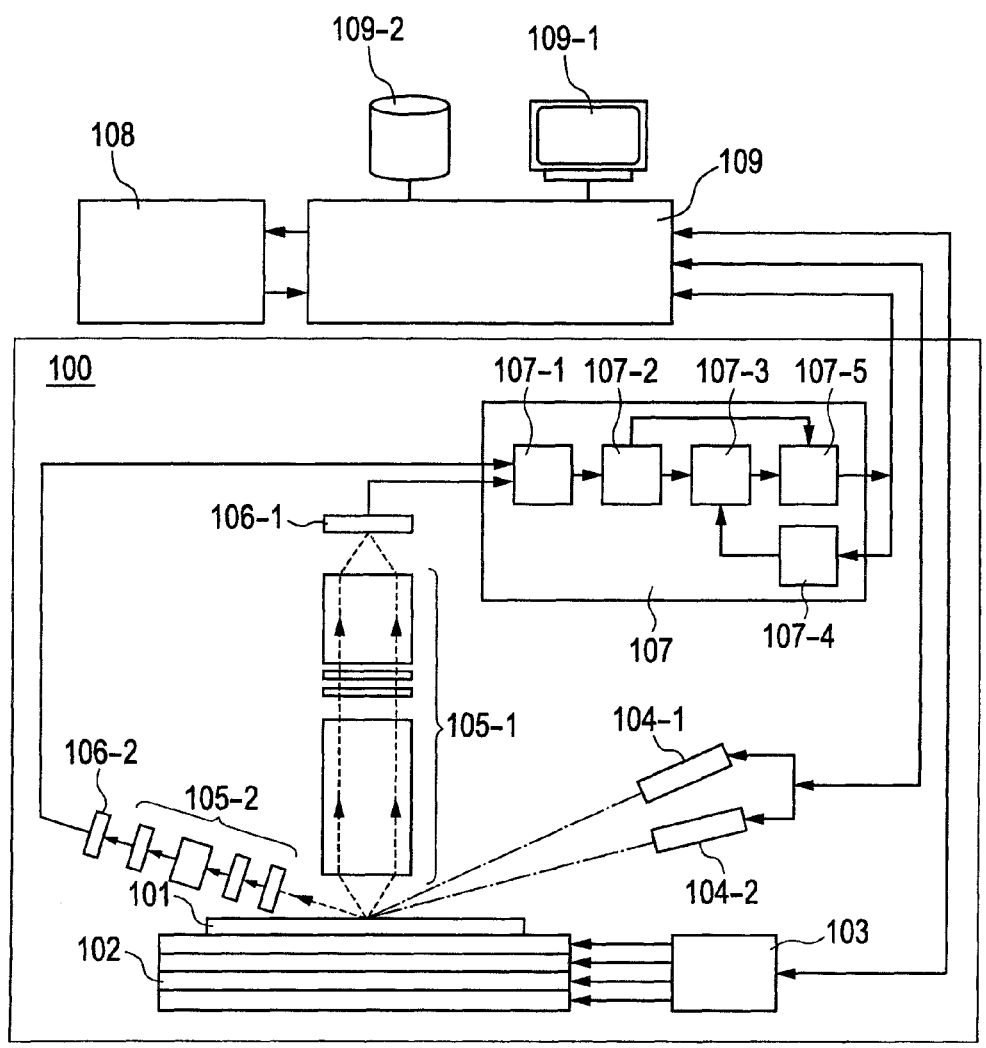
FIG. 13 is a diagram showing an exemplary arrangement of a defect inspection device according to a second embodiment of the invention.

FIG. 13 is a diagram showing an exemplary arrangement of a defect inspection device according to a second embodiment of the invention. The figure shows an example where the defect inspection device using the dark field illumination shown in FIG. 1 is provided with two illumination optical systems and two detection optical systems. The device includes: illumination optical systems 104-1, 104-2; an upper detection system (detection optical system) 105-1; an oblique detection system (detection optical system) 105-2; and image sensors 106-1, 106-2. The defect inspection device further includes an image comparison processing unit 107 (preprocessing unit 107-1, image memory 107-2, defect candidate detection unit 107-3, parameter setting unit 107-4, clipped image creation unit 107-5) and the like. The multiple illumination units 104-1, 104-2 illuminate the sample 101 with lights under mutually different conditions (e.g., illumination angle, illumination direction, illumination wavelength, polarization state and the like). Scattered light from the sample 101 is focused into an image by the upper detection system (detection optical system) 105-1 or the oblique detection system (detection optical system) 105-2. The focused optical image is captured by the respective image sensors 106-1, 106-2 so as to be converted into an image signal. Defect candidates are detected from an image captured under a combination of two or more conditions including one from the illumination conditions and one from the detection conditions. The defect candidates so detected can be classified into 'DOI' or 'Nuisance' by the post-inspection processing unit.

At this time, the feature quantity selection unit automatically selects a feature quantity effective for the classification from the feature quantities extracted from the image captured under the combination of two or more different conditions. This selection is equivalent to an automatic determination of optical condition effective for the classification.

Third Embodiment

Still another embodiment of the defect inspection device including the image processing system having the above-described structure is described by way of example where the inspection device includes an optical system capable of illuminating light having multiple wavelengths, and detection optical systems that can receive discrete lights having different wavelengths respectively.

Figure 14:
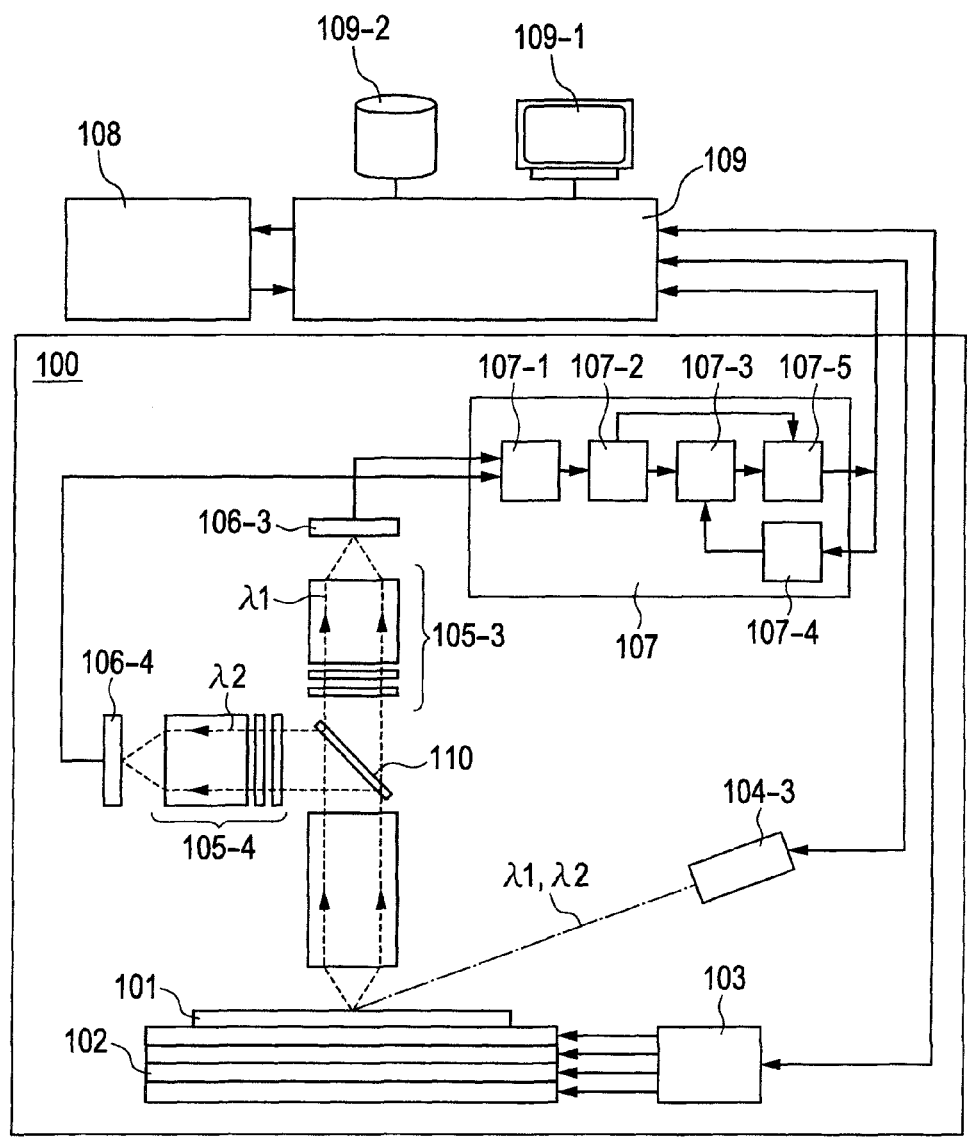
FIG. 14 is a diagram showing an exemplary arrangement of a defect inspection device according to a third embodiment of the invention.

FIG. 14 is a diagram showing an exemplary arrangement of a defect inspection device according to a third embodiment of the invention. The figure illustrates an example where the defect inspection device using the dark field illumination shown in FIG. 1 is provided with an illumination optical system capable of illuminating light having different wavelengths and detection optical systems that can receive discrete lights having different wavelengths respectively. An illumination unit 104-3 illuminates the sample 101 with light having different wavelengths (e.g., $\lambda 1, \lambda 2$). Scattered light from the sample 101 is split by a dichroic mirror 110 or the like while the split light beams are focused into images by detection systems (detection optical systems) 105-3, 105-4. The resultant optical images are received by respective image sensors 106-3, 106-4 to be converted into respective image signals. Defect candidates are detected from the optical images captured by the detection systems adapted to receive light at respectively different wavelengths under respective combinations of at least two different conditions. The detected defect candidates can be classified into 'DOI' or 'Nuisance' by the post-processing.

At this time, the feature quantity selection unit automatically selects the feature quantity effective for the classification from the feature quantities of the images captured under respective combinations of two or more different conditions. This selection is equivalent to the automatic determination of optical conditions effective for the classification.

Fourth Embodiment

Still another embodiment of the defect inspection device including the image processing system having the above-described structure is described by way of example where the inspection device includes a plurality of illumination systems for illuminating different areas and a plurality of detection systems for simultaneously capturing optical images from the different areas.

Figure 15:
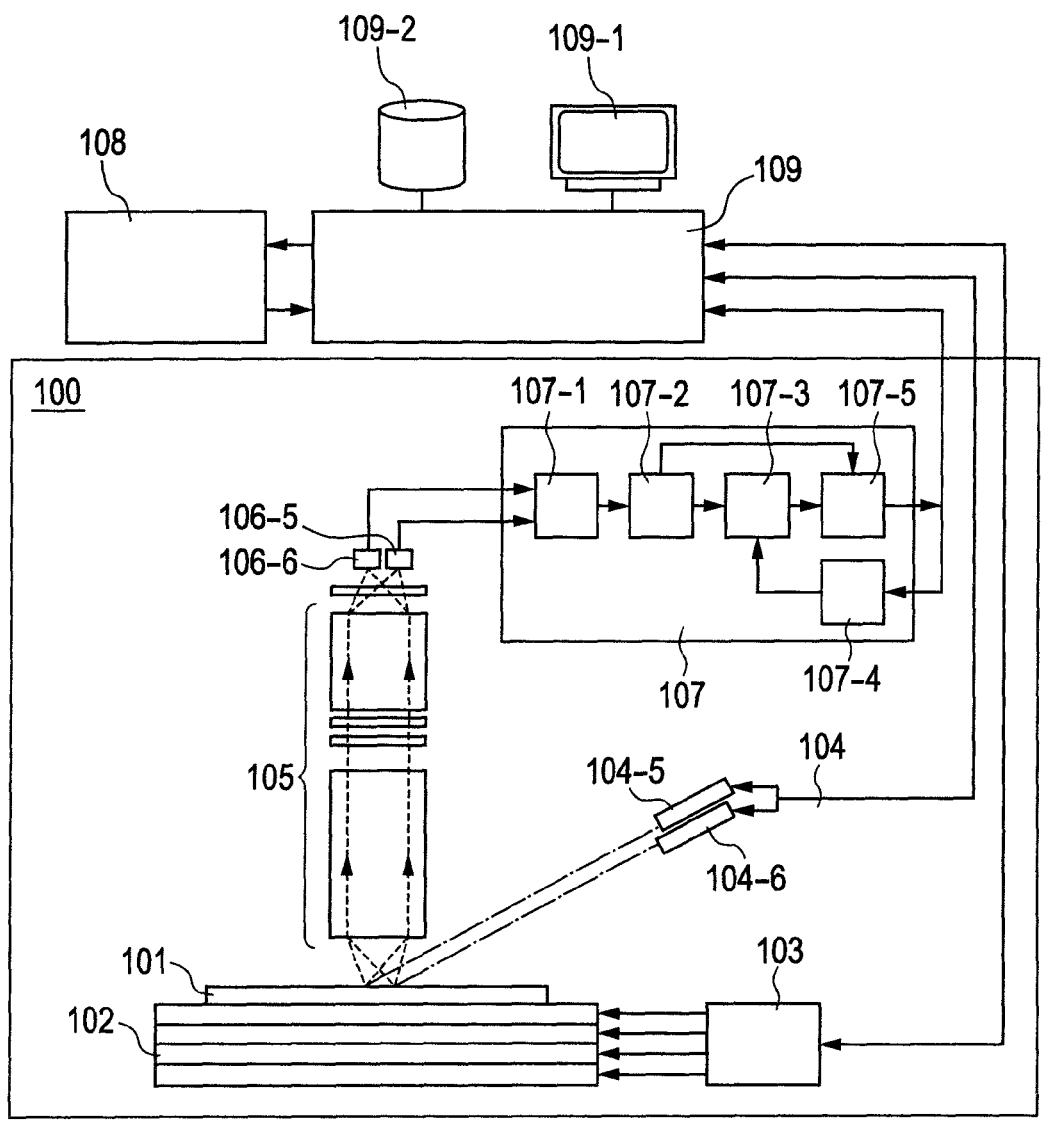
FIG. 15 is a diagram showing an exemplary arrangement of a defect inspection device according to a fourth embodiment of the invention.

FIG. 15 is a diagram showing an exemplary arrangement of a defect inspection device according to a fourth embodiment of the invention. Two illumination optical systems 104-5, 104-6 simultaneously illuminate multiple areas for illumination of the sample 101 with light. Scattered lights from the sample 101 are focused into images by the detection optical system (upper detection system) 105. The resultant optical images of the respective areas are received by image sensors 106-5, 106-6 to be converted into image signals, respectively. The defect candidates are detected as follows. The images detected from the respective areas are aligned and merged. Defect candidates are detected from the resultant image. The detected defect candidates can be classified into 'DOI' or 'Nuisance' by the post-processing.

At this time, the feature quantity selection unit automatically selects the feature quantity effective for the classification from the feature quantities of the images captured under the respective combinations of two or more different conditions. This selection is equivalent to the automatic determination of optical condition effective for the classification.

While the above first to fourth embodiments illustrate the example where the defect candidates are classified into 'DOI' and 'Nuisance', the invention is also applicable to classification into two or more defect types (scratch, foreign substance, bridge and the like) as well as to any kinds of classifications such as into fatal and nonfatal, and real defect and false defect.

In the above first to fourth embodiments, the description is made on the inspection of the semiconductor device as the subject of the invention. However, the subject of the invention is not limited to this and is also applicable to any subjects such as a fabrication process for TFT panel and the evaluation thereof, defect inspection of fabrication process for GMR head for hard disk and the evaluation thereof, and defect inspection and evaluation of printed circuit board.

While the above embodiments illustrate the dark field defect inspection devices, the invention is applicable to all types of inspection apparatuses such as bright field inspection devices and SEM inspection devices.

REFERENCE SIGNS LIST

100: defect candidate detection unit
101: sample
102: stage
103: mechanical controller
104: illumination optical system
105: upper detection system (detection optical system)
111: spatial frequency filter
112: photodetector
106: image sensor
107: image comparison processing unit
107-1: preprocessing unit
107-2: image memory
107-3: defect candidate detection unit
107-4: parameter setting unit
107-5: clipped image creation unit
109: main control unit
109-1: user interface
109-2: recording unit
115: defect detection unit
307: defect candidate
307-1: value feature
307-2: detection image
307-3: reference image
404: defect classification calculation unit
406: classification boundary
407: result display unit
408: instruction input unit
409: termination determination input unit
501: defect feature quantity calculation unit
502: defect candidate grouping unit
503: defect classification evaluation value calculation unit
504: defect matrix creation unit
505: defect classification evaluation value updating unit
506: defect classification threshold determination unit
601: defect candidate window

The invention claimed is:

1. A defect inspection device comprising:
an illumination optical system for illuminating a sample with light;
a detection optical system for detecting scattered light from the sample illuminated by the illumination optical system; and
a processing unit configured to detect a defect on the basis of the scattered light detected by the detection optical system,
wherein the processing unit includes:
a defect feature quantity calculation unit configured to calculate a feature quantity of each defect candidate extracted on the basis of the scattered light detected by the detection optical system;
a defect candidate grouping unit configured to perform grouping of the defect candidates on the basis of the feature quantity calculated by the detect feature quantity calculation unit;
a defect classification evaluation value calculation unit configured to calculate a defect classification evaluation value of the defect candidate on the basis of a feature quantity selected from the feature quantity calculated by the defect feature quantity calculation unit;
a defect classification evaluation value updating unit configured to update the defect classification evaluation value calculated by the defect classification evaluation value calculation unit by teaching a defect candidate which is selected from the defect candidates based on a first classification boundary which is a threshold for classify the defect candidates;
a defect classification threshold determination unit configured to determine, on the basis of the defect classification evaluation value updated by the defect classification evaluation value updating unit, a second classification boundary as a threshold for classification of the defect candidates into defect types; and
a defect detection unit configured to detect a defect using the second classification boundary determined by the defect classification threshold determination unit;
wherein the defect feature quantity calculation unit, the defect candidate grouping unit, the defect classification evaluation value calculation unit, the defect classification evaluation value updating unit, the defect classification threshold determination unit and the defect detention unit are effected by a hardware processor.

2. The defect inspection device according to claim 1, wherein the defect classification evaluation value updating unit configured to perform at least one of adding the teaching of the defect candidate selected by using the first classification boundary or re-selecting the evaluation value calculated by the defect feature quantity calculation unit.

3. The defect inspection device according to claim 1, wherein the defect candidate grouping unit configured to perform grouping of the defect candidates using at least one of background image similarity of the defect candidates, proximity between the defect candidates, and configuration similarity of the defect candidates.

4. The defect inspection device according to claim 1, wherein the defect feature quantity calculation unit configured to calculate the feature quantity on the basis of the defect candidate and an image corresponding to a signal based on the scattered light or a value feature.

5. The defect inspection device according to claim 1, wherein the defect classification evaluation value calculation unit configured to integrate the feature quantities, which is selected for each group configured to determine by the defect candidate grouping unit, and to calculate the defect classification evaluation value.

6. A defect inspection method comprising:
an illumination step of illuminating a sample with light;
a detection step of detecting scattered light from the sample illuminated by the illumination step with a sensor; and
the processing step including:
a defect feature quantity calculation step of calculating a feature quantity of each defect candidate extracted on the basis of the scattered light detected by the detection step;
a defect candidate grouping step of grouping the defect candidates on the basis of the feature quantity calculated by the defect feature quantity calculation step;
a defect classification evaluation value calculation step of calculating a defect classification evaluation value of the defect candidate on the basis of the feature quantity calculated by the defect feature quantity calculation step;
a defect classification evaluation value updating step of updating the defect classification evaluation value calculated by the defect classification evaluation value calculation step by teaching a defect candidate which is selected from the defect candidates based on a first classification boundary which is a threshold for classify the defect candidates;
a defect classification threshold determination step of determining, on the basis of the defect classification evaluation value updated by the defect classification evaluation value updating step, a second classification boundary as a threshold for classifying the defect candidates into defect types; and
a defect detection step of detecting a defect using the second classification boundary determined by the defect classification threshold determination step.

7. The defect inspection method according to claim 6, wherein in the defect classification evaluation value updating step, performing at least one of adding the teaching of the defect candidate selected by using the first classification boundary or re-selecting the evaluation value calculated in the defect classification evaluation value calculation step.

8. The defect inspection method according to claim 6, wherein in the defect candidate grouping step, grouping of the defect candidates is performed by using at least one of similarity of background image of the defect candidates, proximity between the defect candidates, and configuration similarity of the defect candidates.

9. The defect inspection method according to claim 6, wherein in the defect feature quantity calculation step, the feature quantity is calculated on the basis of an image corresponding to a signal based on the scattered image or a value feature.

10. The defect inspection method according to claim 6, wherein in the defect classification evaluation value calculation step, integrating the feature quantities, which is selected for each group determined in the defect candidate grouping step, and calculating the defect classification evaluation value.

11. A defect inspection device comprising:
an illumination optical system for illuminating a sample with light;
a detection optical system for detecting scattered light from the sample illuminated by the illumination optical system; and
a processing unit configured to detect a defect on the basis of the scattered light detected by the detection optical system,
wherein the processing unit includes:
a defect candidate detection unit configured to extract a defect candidate on the basis of the scattered light detected by the detection optical system;
a defect feature quantity calculation unit configured to calculate at least one feature quantity of each defect candidate extracted by the defect candidate detection unit;
a defect candidate grouping unit configured to perform grouping of the defect candidates on the basis of the feature quantity calculated by the defect feature quantity calculation unit;
a defect classification evaluation value calculation unit configured to calculate a defect classification evaluation value of the defect candidate on the basis of a feature quantity selected from the feature quantity calculated by the defect feature quantity calculation unit;
a defect classification evaluation value updating unit configured to update the defect classification evaluation value for each of the grouped defect candidates calculated by the defect classification evaluation value calculation unit by teaching a defect candidate which is selected from the defect candidates based on a first classification boundary which is a threshold for classify the defect candidates;
a defect classification boundary determination unit configured to determine a second classification boundary for each of the grouped defect candidates on the basis of the evaluation value updated by the defect classification evaluation value updating unit, the classification boundary used for classification of the defect candidates; and
a defect detection unit configured to detect a defect using the second classification boundary determined by the defect classification boundary determination unit,
wherein the defect candidate detection unit, the defect feature quantity calculation unit, the defect candidate grouping unit, the defect classification evaluation value calculation unit, the defect classification evaluation value updating unit, the defect classification boundary determination unit and the defect detection unit are effected by a hardware processor.

12. The defect inspection device according to claim 11, wherein the defect classification evaluation value updating unit configured to perform at least one of addition of the instruction-defined defect and reselection of the feature quantity, and
wherein the processing unit further includes:
a classification performance calculation unit configured to estimate whether or not the classification performance is improved by the classification evaluation value updated by the defect classification evaluation value updating unit, and
a determination unit configured to determine whether to perform the addition of the instruction-defined defect and whether to perform the reselection of the feature quantity, the determination made on the basis of the estimated performance outputted by the classification performance calculation unit;

wherein the classification performance calculation unit and the determination unit are effected by the hardware processor.

13. The defect inspection device according to claim 12, wherein the determination unit configured to automatically determine whether to perform the addition of the instruction-defined defect and whether to perform the reselection of the feature quantity.

14. The defect inspection device according to claim 11, wherein the processing unit configured to evaluate similarity by comparing the defect candidate detected by the defect candidate detection unit with the stored defect candidate group representing at least one of the sample's type, the fabrication process and the feature quantity distribution.

15. The defect inspection device according to claim 2, wherein the processing unit including:
- a classification performance calculation unit which configured to calculate a classification performance of a defect classification evaluation value updated by the defect classification evaluation value updating unit;
- a judging unit configured to judge a need of the adding the teaching of the defect candidate or the re-selecting the evaluation value by the classification performance calculated by the classification performance calculation unit;
- a feature quantity selection unit configured to select a feature quantity by the addition of the teaching of the defect candidate in a case when the judging unit judges the need of adding.

16. The defect inspection device according to claim 1, wherein the processing unit including:
- a memory unit configured to store at least one of a criteria for grouping the defect candidates by the defect candidate grouping unit, a feature quantity calculated by the feature quantity calculation unit, a classification boundary calculated by the defect classification evaluation value calculation unit, and a taught defect candidate,
- wherein the processing unit configured to search at least one of the criteria for grouping the defect candidates, the feature quantity, the classification boundary, and the taught defect candidate stored in the memory unit.

17. The defect inspection device according to claim 16, wherein the processing unit configured to search the memory unit by using information on the sample of varieties or process, similarity of the feature distribution of defect candidates detected by the processing unit and similarity of the image, and using the search information in classifying the defect candidates.

18. The defect inspection method according to claim 6, wherein the step of processing including:
- a classification performance calculation step of calculating a classification performance of a defect classification evaluation value updated in the defect classification evaluation value updating step;
- a judging step of judging a need of the adding the teaching of the defect candidate or the re-selecting the evaluation value by the classification performance calculated in the classification performance calculation step;
- a feature quantity selection step of selecting a feature quantity by the addition of the teaching of the defect candidate in a case when the need of adding is judges in the judging step.

19. The defect inspection method according to claim 6, wherein the step of processing including:
- storing step of storing in a memory at least one of a criteria for grouping the defect candidates in the defect candidate grouping step, a feature quantity calculated in the feature quantity calculation step, a classification boundary calculated in the defect classification evaluation value calculation step, and a taught defect candidate,
- wherein the step of processing, searching at least one of the criteria for grouping the defect candidates, the feature quantity, the classification boundary, and the taught defect candidate stored in the memory in the storing step.

20. The defect inspection method according to claim 19, wherein the processing step, searching the memory is performed by using information on the sample of varieties or process, similarity of the feature distribution of defect candidates detected by the processing unit and similarity of the image, and using the search information in classifying the defect candidates.

* * * * *